(12) United States Patent
Garigapati et al.

(10) Patent No.: US 12,097,306 B2
(45) Date of Patent: Sep. 24, 2024

(54) CONFORMAL COATING OF BIOLOGICAL SURFACES

(71) Applicant: Takeda Pharmaceutical Company Limited, Osaka (JP)

(72) Inventors: Venkat R. Garigapati, Southborough, MA (US); Tetsuya Matsuura, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 179 days.

(21) Appl. No.: 16/467,524

(22) PCT Filed: Dec. 13, 2017

(86) PCT No.: PCT/US2017/066072
§ 371 (c)(1),
(2) Date: Jun. 7, 2019

(87) PCT Pub. No.: WO2018/112026
PCT Pub. Date: Jun. 21, 2018

(65) Prior Publication Data
US 2019/0365955 A1    Dec. 5, 2019

Related U.S. Application Data

(60) Provisional application No. 62/433,449, filed on Dec. 13, 2016.

(51) Int. Cl.
| | | |
|---|---|---|
| *A61L 27/52* | (2006.01) | |
| *A61L 27/16* | (2006.01) | |
| *A61L 27/18* | (2006.01) | |
| *A61L 27/26* | (2006.01) | |
| *A61L 27/38* | (2006.01) | |
| *A61L 27/54* | (2006.01) | |

(52) U.S. Cl.
CPC ............... *A61L 27/52* (2013.01); *A61L 27/16* (2013.01); *A61L 27/18* (2013.01); *A61L 27/26* (2013.01); *A61L 27/3804* (2013.01); *A61L 27/3834* (2013.01); *A61L 27/54* (2013.01); *A61L 2420/02* (2013.01)

(58) Field of Classification Search
CPC .......... A61L 27/52; A61L 27/16; A61L 27/18; A61L 27/26; A61L 27/3804; A61L 27/3834; A61L 27/54; A61L 2420/02
See application file for complete search history.

(56) References Cited

U.S. PATENT DOCUMENTS

| | | |
|---|---|---|
| 5,837,747 A | 11/1998 | Soon-Shiong et al. |
| 6,224,893 B1 | 5/2001 | Langer et al. |
| 6,497,902 B1 | 12/2002 | Ma |
| 6,642,363 B1 | 11/2003 | Mooney et al. |
| 7,824,672 B2 | 11/2010 | Chaikof et al. |
| 8,216,558 B2 | 7/2012 | Van et al. |
| 8,591,950 B2 | 11/2013 | Bennett et al. |
| 11,655,343 B2 | 5/2023 | Garigapati et al. |
| 2002/0037308 A1 | 3/2002 | Sefton et al. |
| 2007/0048291 A1 | 3/2007 | Mang et al. |
| 2009/0220607 A1 | 9/2009 | Kiser et al. |
| 2010/0143464 A1 | 6/2010 | Stabler et al. |
| 2011/0111033 A1 | 5/2011 | Stover et al. |
| 2014/0147483 A1 | 5/2014 | Hubbell et al. |
| 2015/0071997 A1 | 3/2015 | Garcia et al. |
| 2015/0290327 A1 | 10/2015 | Zenobi-Wong et al. |
| 2017/0182220 A1* | 6/2017 | Song ...................... A61L 27/18 |
| 2017/0189581 A1 | 7/2017 | Desai et al. |
| 2017/0313827 A1 | 11/2017 | Zhu et al. |
| 2019/0100628 A1 | 8/2019 | Garigapati et al. |
| 2023/0348675 A1 | 11/2023 | Garigapati et al. |

FOREIGN PATENT DOCUMENTS

| | | |
|---|---|---|
| CA | 2837558 C | 11/2018 |
| CN | 1703175 A | 11/2005 |
| CN | 102164580 A | 8/2011 |
| CN | 102239248 A | 11/2011 |
| CN | 104292454 A | 1/2015 |
| CN | 104487093 A | 4/2015 |
| CN | 104530441 A | 4/2015 |
| JP | 11-509833 A | 8/1999 |
| JP | 2001-524136 A | 11/2001 |
| JP | 2006-503080 A | 1/2006 |
| JP | 2009-535453 A | 10/2009 |
| JP | 2011-246714 A | 12/2011 |
| JP | 6829898 B2 | 2/2021 |
| WO | WO 94/12161 A1 | 6/1994 |
| WO | 98/12228 A1 | 3/1998 |
| WO | WO 2004/032881 A2 | 4/2004 |

(Continued)

OTHER PUBLICATIONS

Feng et al., Acta Biomaterialia 7 (2011) 3692-3699. (Year: 2011).*
International Search Report for PCT/US2017/066072, mailed Mar. 15, 2018, 3 pages.
No Author Listed, Examination Handbook of Patent and Utility Model in Japan. Part II, Chapter 2, sections 2203-2205. pp. 8-23.
Liu et al., Biodegradable poly(ethylene glycol)-peptide hydrogels with well-defined structure and properties for cell delivery. Biomaterials. Mar. 2009;30(8):1453-61. doi: 10.1016/j.biomaterials.2008.11.023. Epub Dec. 20, 2008.
Van Dijk et al., Synthesis and characterization of enzymatically biodegradable PEG and peptide-based hydrogels prepared by click chemistry. Biomacromolecules. Jun. 14, 2010;11(6):1608-14. doi: 10.1021/bm1002637.
Patel et al., Development and evaluation of a calcium alginate based oral ceftriaxone sodium formulation. Prog Biomater. 2016;5:117-133. doi: 10.1007/s40204-016-0051-9. Epub Jul. 20, 2016.

(Continued)

*Primary Examiner* — Robert S Cabral
(74) *Attorney, Agent, or Firm* — Wolf, Greenfield & Sacks, P.C.

(57) ABSTRACT

The invention provides, inter alia, ultra-thin conformal coated biological surfaces, such as living cells, cell clusters, tissues, organs, and hybrid synthetic organs, and methods of making the same, e.g., using click reactive water soluble polymers, under conditions that do not damage or significantly modify the biological surfaces. In some embodiments, the coated biological surfaces are suitable for delivery to a subject in need thereof.

22 Claims, 25 Drawing Sheets

(56) References Cited

FOREIGN PATENT DOCUMENTS

| WO | 2007/127277 A2 | 11/2007 |
|---|---|---|
| WO | 96/31199 A1 | 10/2009 |
| WO | WO 2010/033611 A1 | 3/2010 |
| WO | WO 2010/064171 A1 | 6/2010 |
| WO | WO 2010/099818 A1 | 9/2010 |
| WO | WO 2014/022501 A2 | 2/2014 |
| WO | 2014/034884 A1 | 3/2014 |
| WO | WO 2014/041231 A1 | 3/2014 |
| WO | 2015/067763 A1 | 5/2015 |
| WO | 2015/130878 A1 | 9/2015 |
| WO | WO 2015/154078 A1 | 10/2015 |
| WO | WO 2016/159380 A1 | 10/2016 |
| WO | 2017/042301 A1 | 3/2017 |
| WO | WO 2017/165389 A2 | 9/2017 |
| WO | WO 2018/112026 A1 | 6/2018 |

OTHER PUBLICATIONS

Zia et al., Alginate-Poly(Ethylene) Glycol and Poly(Ethylene) Oxide Blend Materials. Chapter 16. Algae Based Polymers, Blends, and Composites. Dec. 2017; 581-601. DOI:10.1016/B978-0-12-812360-7.00016-1.

Xiaodong, Li, et al., "A novel system for water soluble protein encapsulation with high efficiency: "Micelles enhanced" polyeletrolyte capsules", Wiley Periodicals, Inc., (2007), pp. 768-776.

Alice A. Tomei, et al., "Device design and materials optimization of conformal coating for islets of Langerhans", PNAS 111 (2014), pp. 10514-10519.

Angelo A. Mao, et al., "Deterministic encapsulation of single cells in thin tunable microgels for niche modelling and therapeutic delivery", Nature Materials, vol. 16, Feb. 2017, pp. 236-245.

Paolo Blasi, et al., "Conformal polymer coatings for pancreatic islets transplantation", International Journal of Pharmaceutics 440, (2013), pp. 141-147.

David W. Green, et al., "Adult stem cell coatings for regenerative medicine", Materials today, vol. 15, (2019), pp. 60-66.

Carlos E. S. Guedes, et al., "Encapsulation of Living Leishmani Promastigotes in Artificial Lipid Vacuoles", Plos One DOI:10.1371/journal pone.0134925, Aug. 4, 2015, pp. 1-12.

Hiroaki Onoe, et al., "Centrifuge-based cell encapsulation in hydrogel microbeads using sub-microliter sample solution", RCA Adv. vol. 4, (2014), pp. 30480-30484.

Joseph J. Richardson, et al., "Fluidized Bed Layer-by-Layer Microapsule Formation", Langmuir vol. 30, (2014), pp. 10028-10034.

Kenneth A. Dawson, et al., "Leukocyte-like carriers", Nature Materials, vol. 15, (2016), pp. 935-936.

Michael Humphrey May, Conformal Coating of Mammalian Cells at a Liquid-Liquid Interface, Canadian Thesis in University of Toronto, May 1998, pp. 1-313.

Maria Jose Martin, "Microencapsulation of bacteria: A review of different technologies and their impact on the probiotic effects", Innocative Food Science and Emerging Technologies, vol. 27 (2015), pp. 15-25.

Sweta Rathore, "Microencapsulation of microbial cells", Journal of Food Engineering, (2013), pp. 369-381.

Kaila Kallasapathy, "Microencapsulation of Probiotic Bacteria: Technology and Potential Applications", Curr. Issues Intest. Microbiol., vol. 3, (2002), pp. 39-48.

Moreau, "Hydrogel films and coatings by swelling-induced gelation", PNAS, vol. 113, No. 47, Nov. 22, 2016, pp. 13295-13300.

Ricardo D.C. Ribeiro, et al., "Temporary Single-Cell Coating for Bioprocessing with a Cationic Polymer", ACS App. Matter, Interfaces 9, (2017), pp. 12967-12974.

Kolb et al., Click Chemistry: Diverse Chemical Function from a Few Good Reactions. Angew Chem Int Ed Engl. Jun. 1, 2001;40(11):2004-2021. doi: 10.1002/1521-3773(20010601)40:11<2004: AID-ANIE2004>3.0.CO;2-5.

Extended European Search Report for Application No. 22184214.9, mailed Feb. 14, 2023.

U.S. Appl. No. 16/086,405, filed Sep. 19, 2018, Garigapati et al.

Dang et al., Biocompatible and antifouling coating of cell membrane phosphorylcholine and mussel catechol modified multi-arm PEGs. J Mater Chem B. Mar. 21, 2015;3(11):2350-2361. doi: 10.1039/c4tb02140a. Epub Feb. 13, 2015.

Yang et al., Phosphorylcholine-containing polymers for use in cell encapsulation. Artif Cells Blood Substit Immobil Biotechnol. Feb. 2004;32(1):91-104. doi: 10.1081/bio-120028671.

Yigit et al., Fabrication and Functionalization of Hydrogels through "Click" Chemistry. Chem Asian J. Oct. 4, 2011;6(10):2648-59. doi: 10.1002/asia.201100440. Epub Aug. 29, 2011.

International Preliminary Report on Patentability mailed Jun. 27, 2019, for Application No. PCT/US2017/066072.

Barker et al., Biodegradable DNA-enabled poly(ethylene glycol) hydrogels prepared by copper-free click chemistry. J Biomater Sci Polym Ed. 2016;27(1):22-39. doi: 10.1080/09205063.2015.1103590. Epub Nov. 6, 2015.

Gattas-Asfura et al., Covalent layer-by-layer assembly of hyperbranched polymers on alginate microcapsules to impart stability and permselectivity. J Mater Chem B. Dec. 14, 2014;2(46):8208-8219.

Guanming et al., Synthesis of Hydrogels via Copper-Free Click Reactions. Progress in Chemistry. 2014; 26(7): 1223-32.

Ma et al., Artificial microniches for probing mesenchymal stem cell fate in 3D. Biomater Sci. Nov. 30, 2014;2(11):1661-1671. doi: 10.1039/c4bm00104d. Epub Jun. 18, 2014.

Mahou et al., Alginate-Poly(ethylene glycol) Hybrid Microspheres with Adjustable Physical Properties. Macromolecules. Jan. 13, 2010;43(3):1371-8.

Xu et al., Cytocompatible poly(ethylene glycol)-co-polycarbonate hydrogels cross-linked by copper-free, strain-promoted click chemistry. Chem Asian J. Oct. 4, 2011;6(10):2730-7. doi: 10.1002/asia.201100411. Epub Aug. 24, 2011.

* cited by examiner

Day 1

Day 3

Day 11

Day 1

Day 8

Day 18

Day 25

Day 38

Day 49

Day 67

Day 1

Day 8

Day 18

Day 26

Day 1, Naked

Day 1, Coated

Day 29, Naked

Day 29, Coated

Scale bar: 100 μm

Fig. 40: Scheme 1
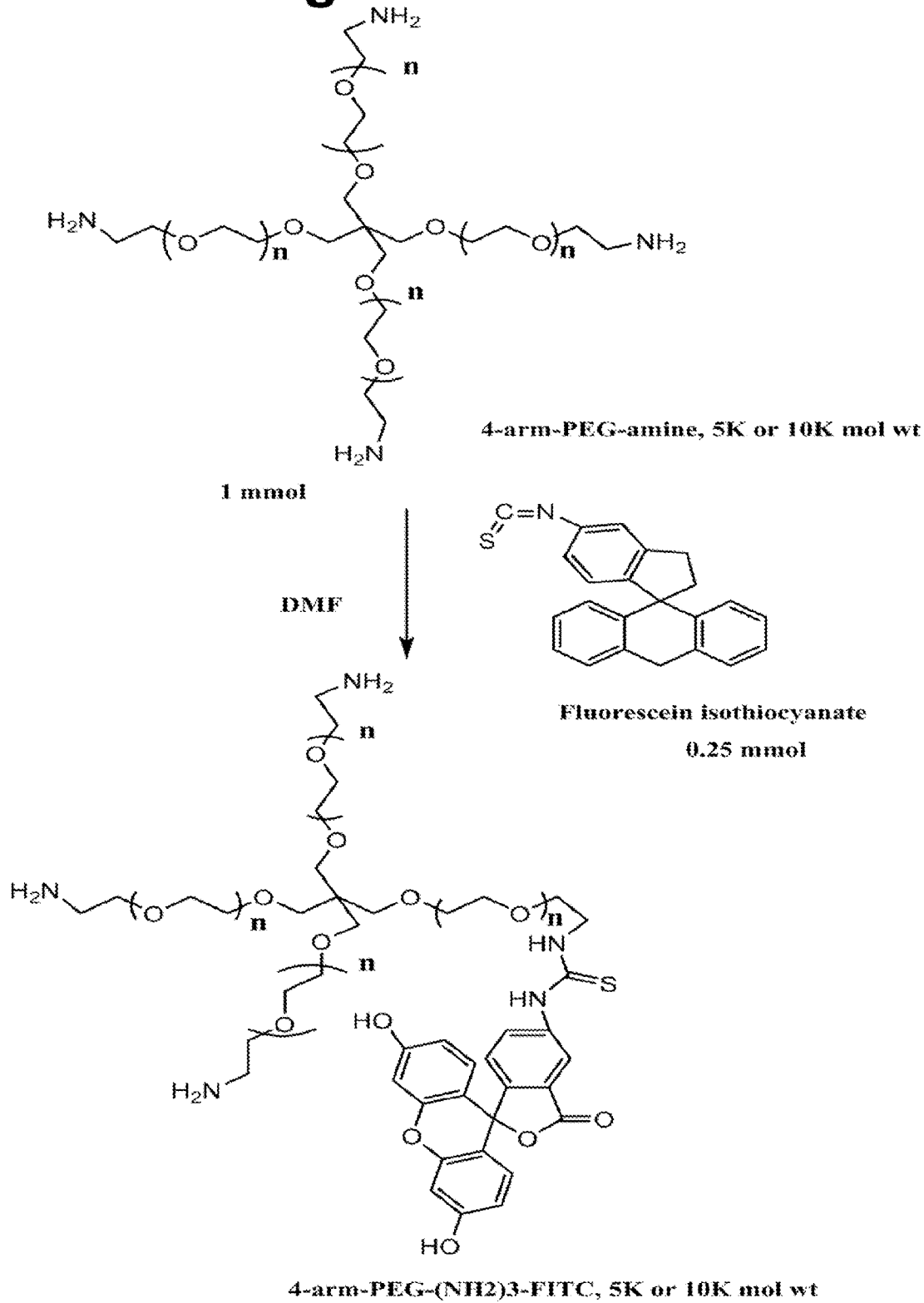
Scheme 1: Synthesis of Fluorescein labeled 4-arm PEG-NH2

Fig. 41: Scheme2
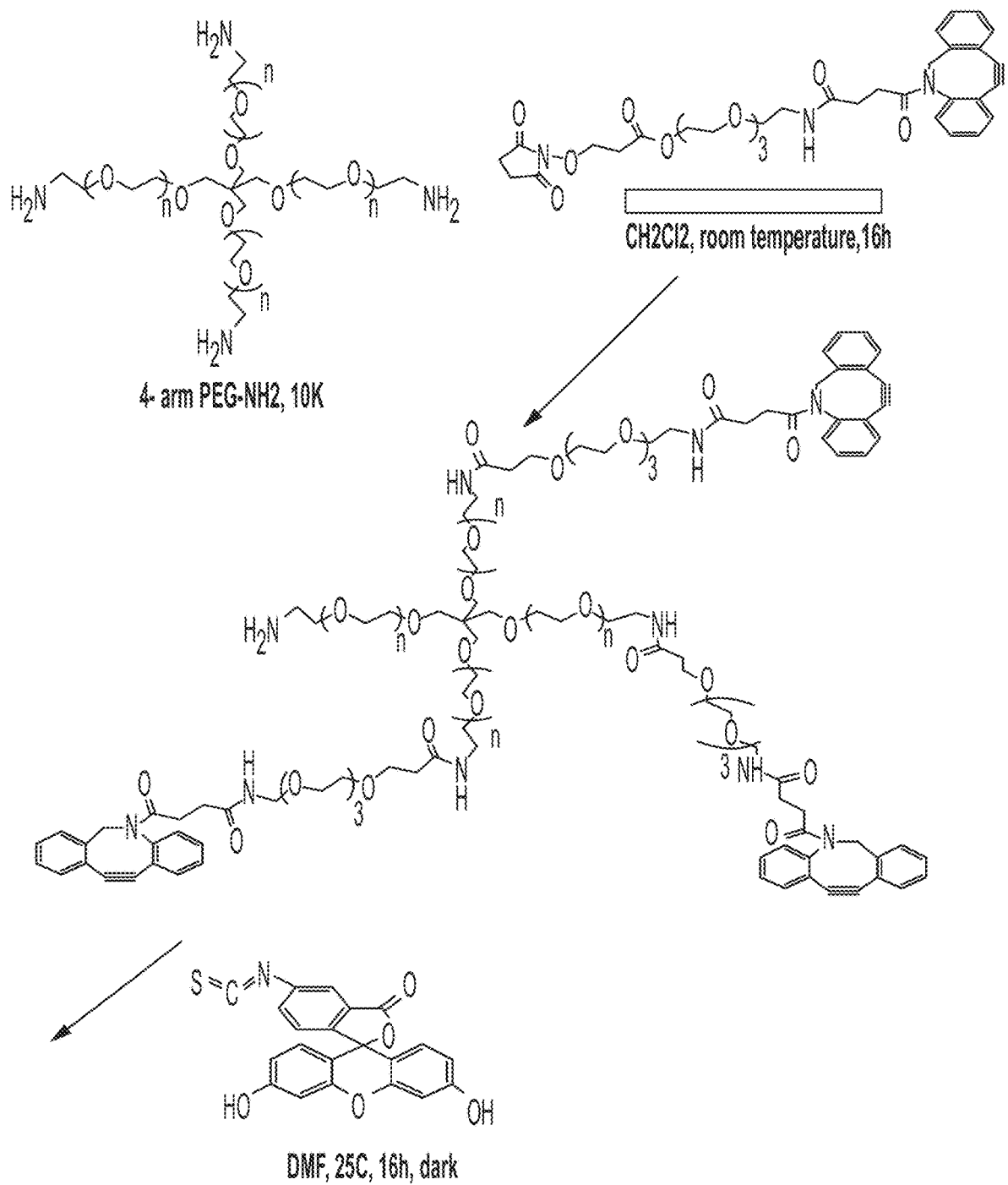

Fig. 41, cont.: Scheme2
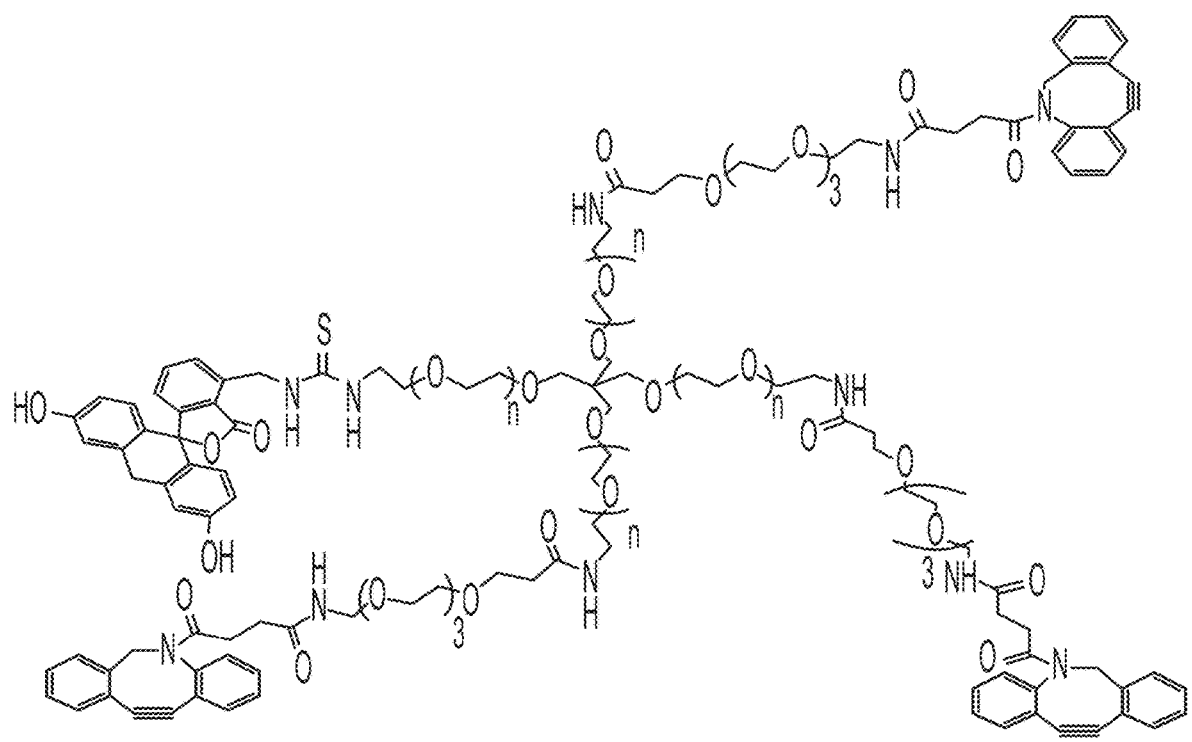
Scheme2: Synthesis of 40Arm-PEG-(NHCO-(PEG)4-DBCO)3-FITC

Fig. 42: Scheme 3
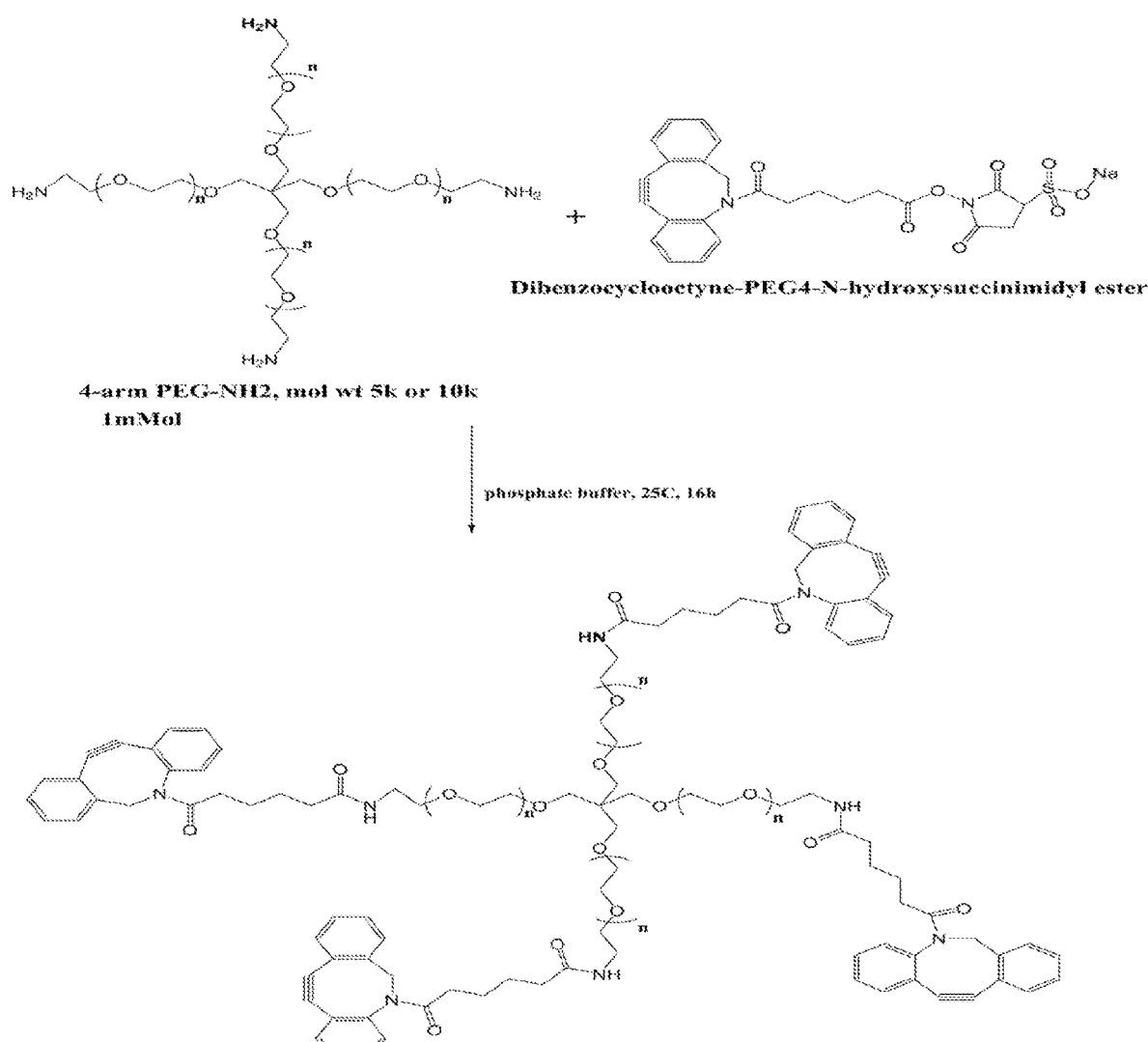

Fig. 43: Scheme 4
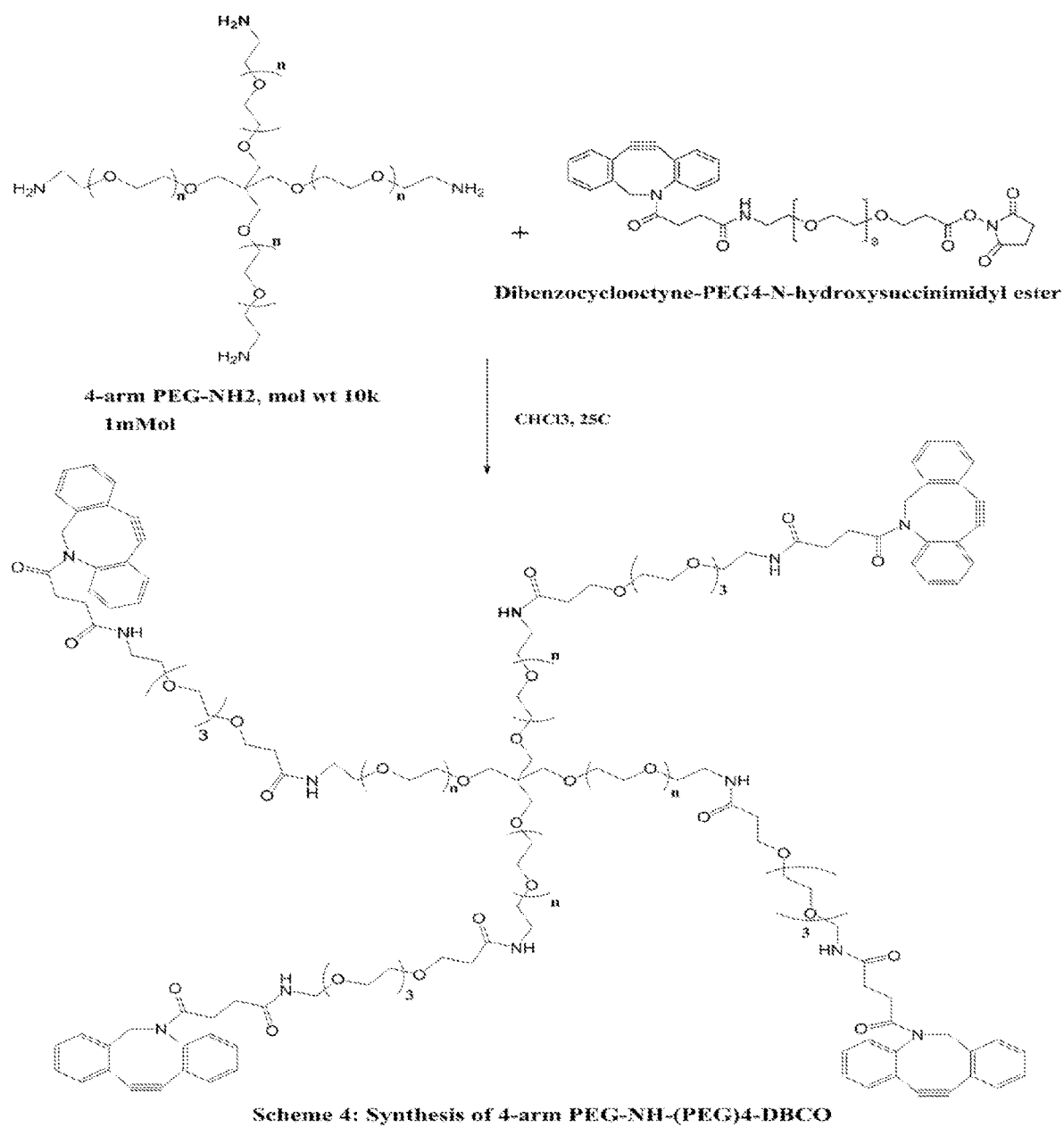

Fig. 44 Scheme 5
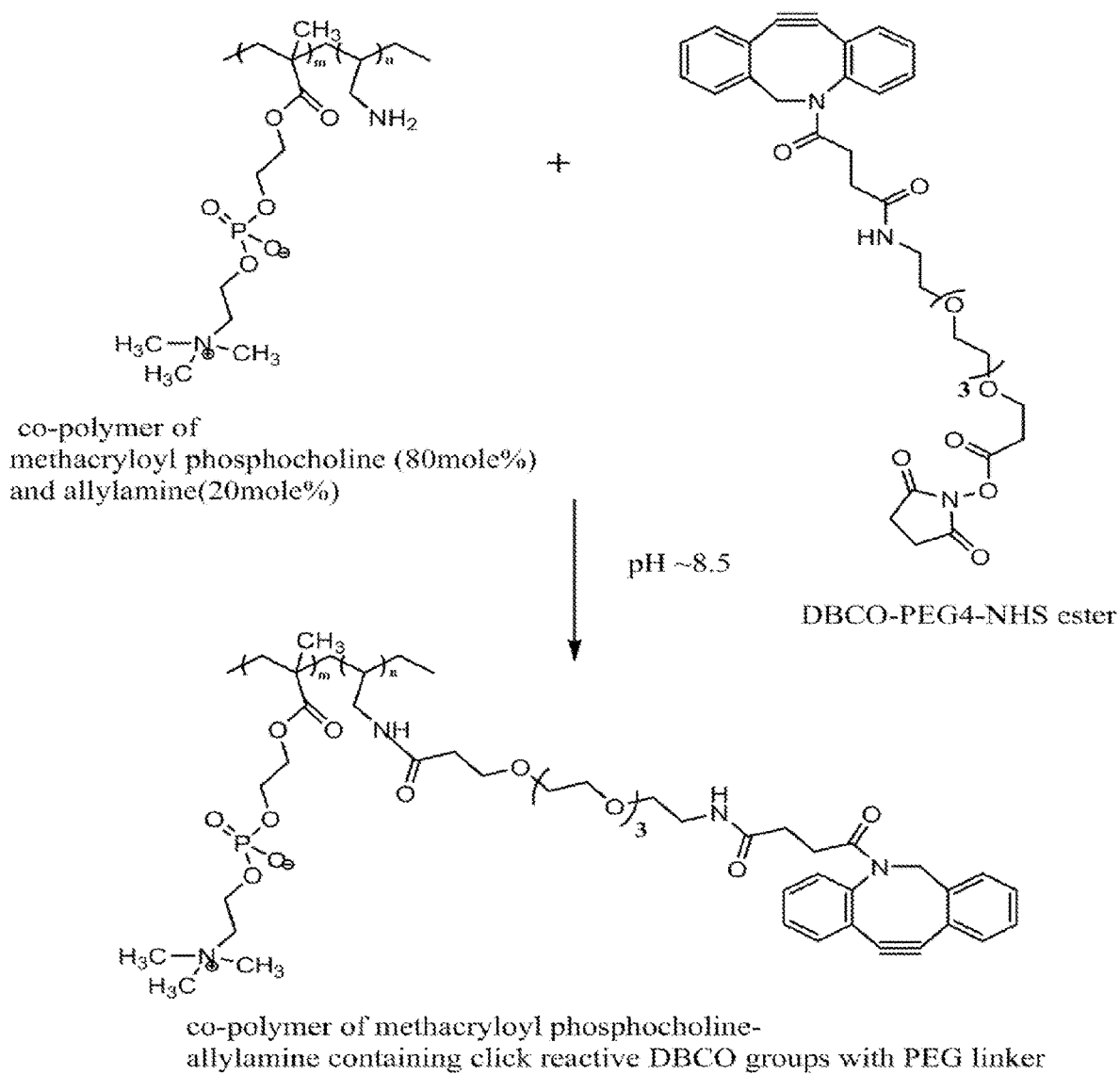

Fig 45: Scheme 6
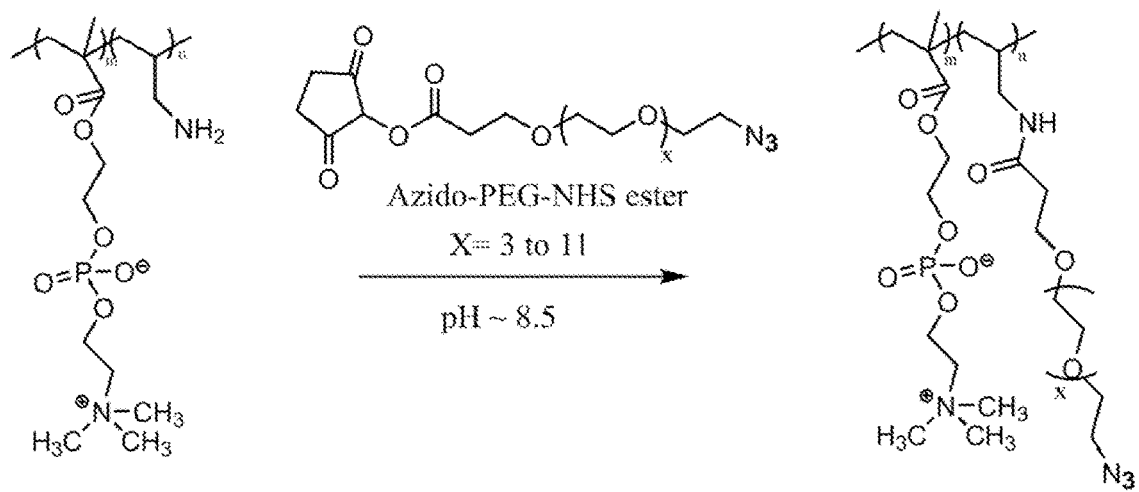

Fig. 46: Scheme 7
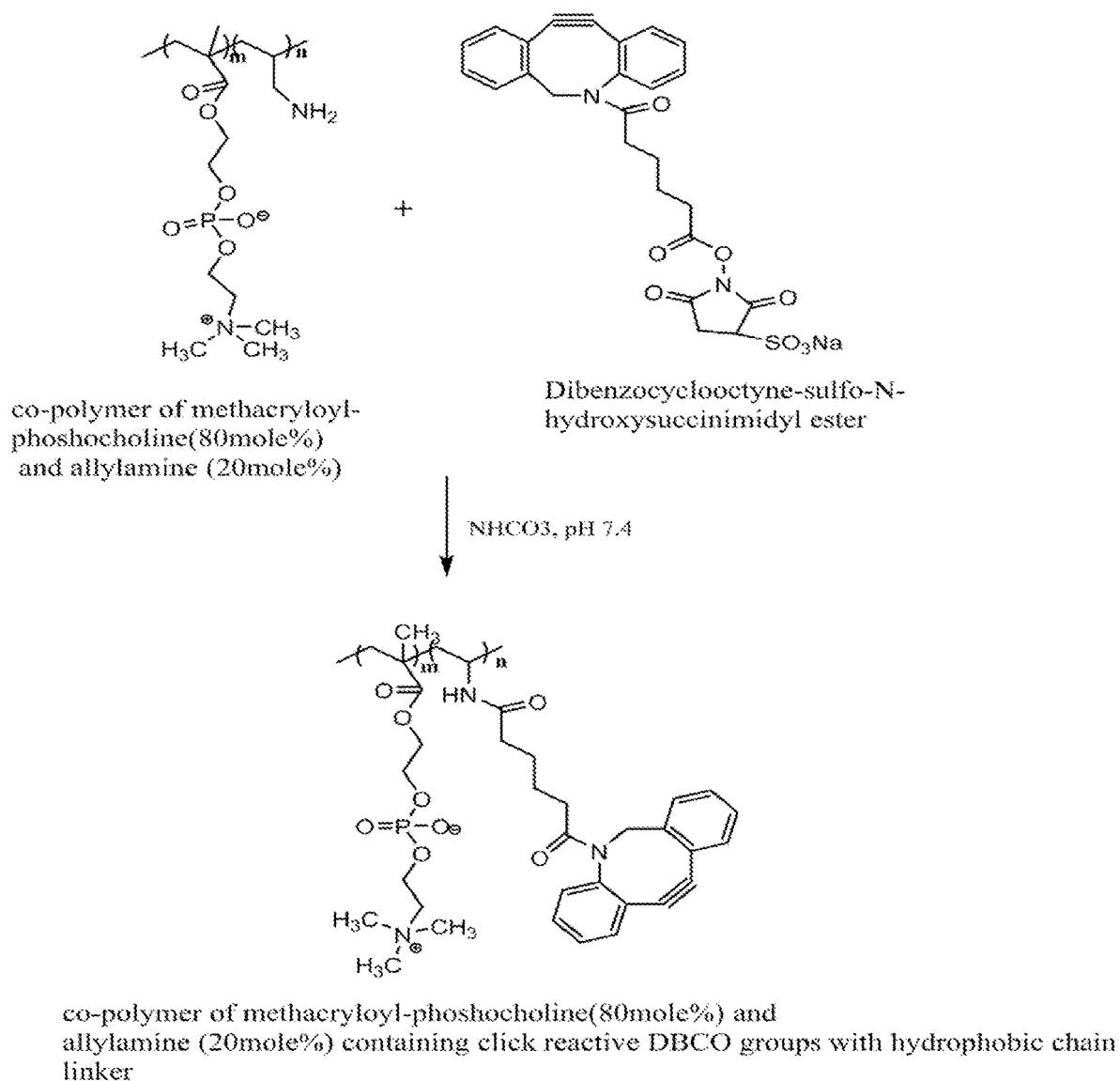

Fig. 47 Scheme 8
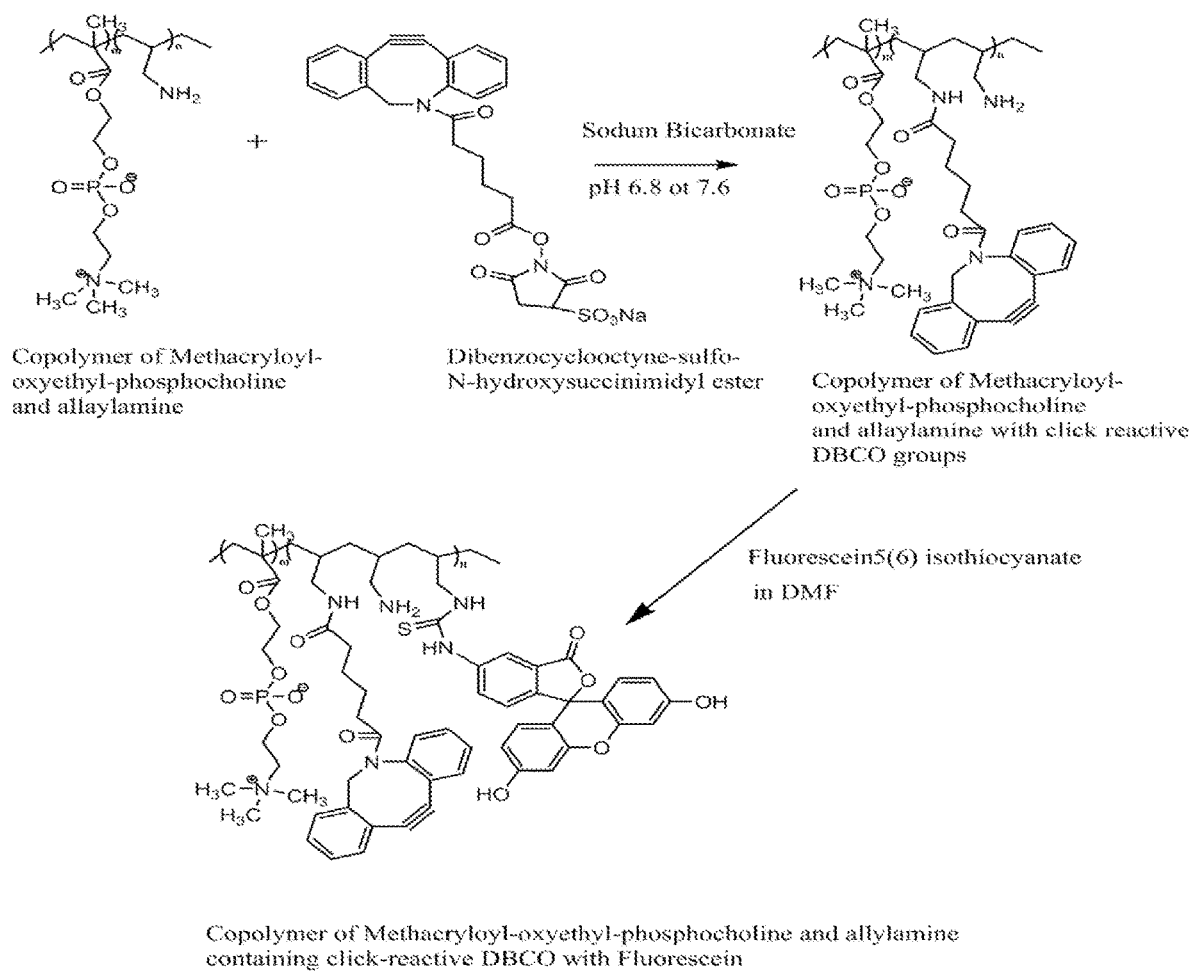

Fig. 48: Scheme 9
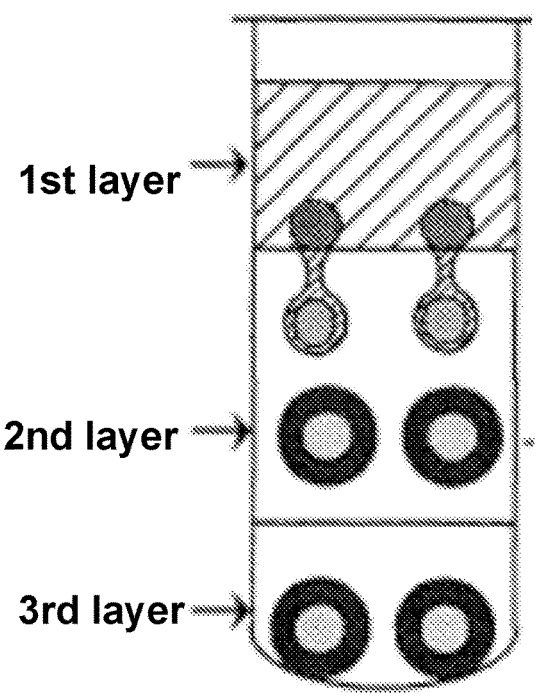
Three Layer Method
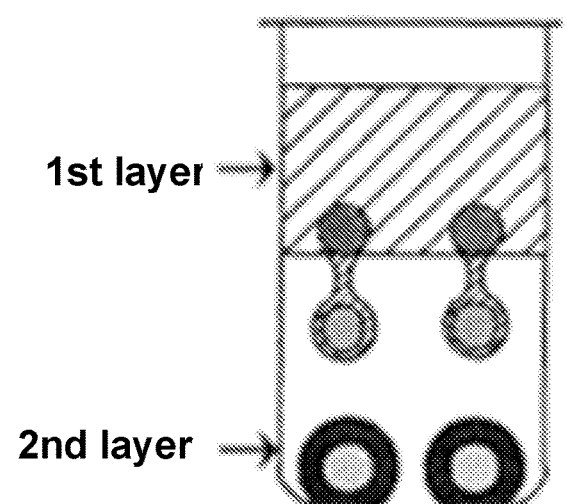
Two Layer Method

Fig. 49: Scheme 10; Diagram for continuous addition method
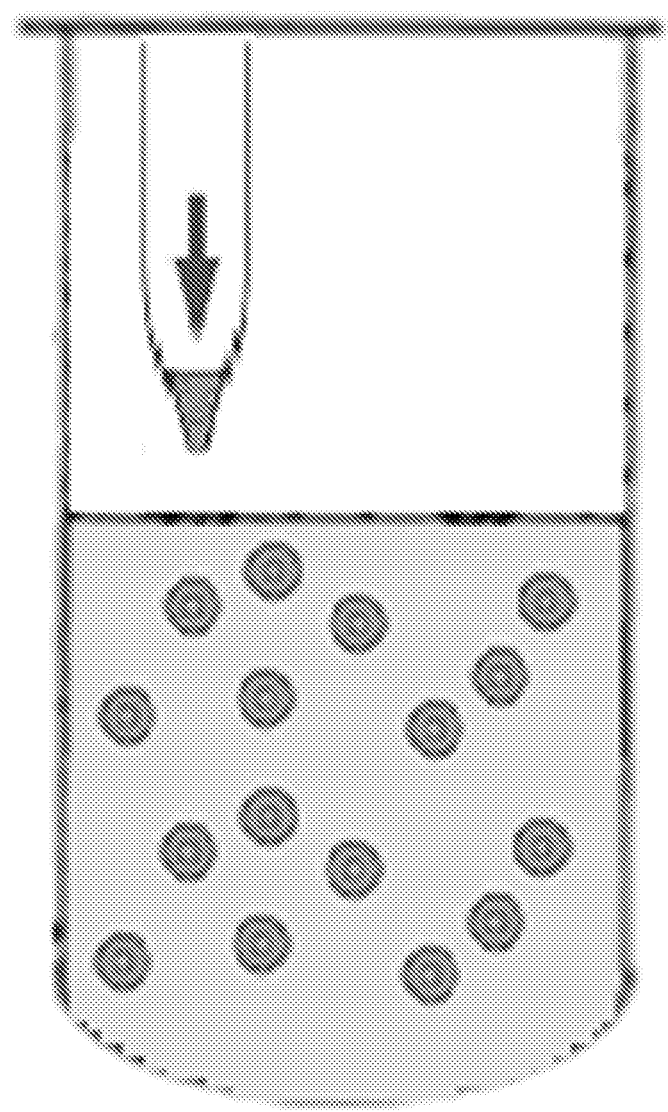

CONFORMAL COATING OF BIOLOGICAL SURFACES

PRIOR APPLICATION

This application is a U.S. National Phase Application of International Application No. PCT/US2017/066072, filed on Dec. 13, 2017, which claims the benefit of U.S. Provisional Application No. 62/433,449, filed Dec. 13, 2016, the complete contents of both of which are incorporated herein by reference. The entire teachings of the foregoing application are incorporated herein by reference.

FIELD OF THE INVENTION

The invention relates to biological surfaces (e.g., cells, cell clusters, tissues, organs, and hybrid synthetic organs) with thin, semi-permeable surfaces-conformally coated biological surfaces, and related methods of making them.

BACKGROUND

Cell-based therapies, such as pancreatic islet transplantation for treating insulin-dependent diabetes, are limited, at least in part, due to underlying host immune system activity. Existing barrier-based methods for isolating the transplanted cells from the host immune system have had limited success. Microencapsulation methods applied to living cells have some serious drawbacks, such as limitations of nutrient and oxygen diffusion because of its size differences and varied random distribution of cells/clusters in the microcapsule environment. These issues usually pose a threat to the function and longevity of cells. Hydrogel conformal coating could overcome the issues which are generally involved in traditional microencapsulation. Some of the theoretical advantages of conformal coating-though not satisfied by existing modalities-include superior nutrient and oxygen supply to cells prolong the life span, improve the drug secreting cell functionality and the opportunity to load high cell doses in small volumes. Despite several advantages to the conformal coating, there are no suitable methods are available to apply to living cells, and existing methods referencing conformal coating are generally very thick and share many of the drawbacks of microencapsulation. Furthermore, existing methods such as two phase systems, emulsion-based methods, and radical/light initiated methods, micro-fluidic methods and liquid/liquid interface methods: 1) modify and produce deleterious effect to the living cells, 2) often form a thick coat greater than 50 to 75 microns, and 3) suffer from reproducibility and scalability. Accordingly, a need exists for biological surfaces-substantially without modification or damage—with conformal coatings and associated methods of making them, which preferably can take place under physiological conditions, and are reproducible, scalable, and deliver superior results.

SUMMARY

The invention provides, inter alia, biological surfaces-substantially without modification or damage—with true conformal coatings and associated methods of making them, methods that can take place under physiological conditions and are reproducible, scalable, and deliver superior results.

A composition provided by the invention will have a conformal coating, such as a hydrogel, that allows the biological surface to retain biological function with little to no damage or modification, e.g., without modification of cell surface molecules, e.g., without covalently conjugating the hydrogel to the biological surface or otherwise modifying the surface, e.g., by disrupting disulfide bonds, or modifying functional carboxylate, amine, or hydroxyl groups, or modifying DNA (e.g., in processes requiring photoactivation), which is inherent in many processes used to embed cells in a matrix. A variety of polymers known to the skilled artisan will be suitable for the hydrogel, including, as exemplified herein, hydrogels formed from, e.g., multi-arm PEG molecules and linear methacryloyloxyethyl co-polymers, e.g., a methacryloyloxyethyl co-polymer with phosphocholine or other zwitterionic group, e.g. a methacryloyloxyethyl co-polymer with phosphocholine and derivatized allylamine (e.g., with appended functional groups, such as click-reactive groups, optionally with intervening linker, to facilitate cross-linkage).

Numerous methodologies to form a composition provided by the invention are described herein. The advantages of the methods provided by the invention include ease, reproducibility, scalability, and physiological compatibility. Biological surfaces, such as cells or cell clusters, are not exposed to harsh conditions and thus maintain superior viability and functionality, while avoiding certain potentially mutagenic steps associated with other coating methods. One advantageous aspect of certain methods provided by the invention is the use of aqueous phases and click-reactive functional groups associated with multi-arm polymers, such as click functional multi-arm PEG molecules, and click functional linear co-polymers based on methacryloyloxyethyl phosphocholine and allylamine (such as the commercially available LIPIDURE®-NH01).

Also, in a related aspect, the compositions provided by the invention can be administered to a subject, such as a human, e.g., in methods of treating or ameliorating a disorder. For example, a disorder (insulin deficiency, such as type 1 diabetes) characterized by a lacking or otherwise deficient biological function (e.g., insulin production) can be treated by administering an effective amount of a composition provided by the invention, such as a composition comprising a conformally coated biological surface (e.g., an insulin-producing cell).

BRIEF DESCRIPTION OF THE DRAWINGS

FIG. 40 is an illustration of Scheme 1 for synthesis of fluorescein labeled 4-arm PEG-NH2.

FIG. 41 is an illustration of Scheme 2 for synthesis of 4 arm-PEG-{NHCO-(PEG)4-DBCO}3-FITC.

FIG. 42 is an illustration of Scheme 3 for synthesis of 4-arm PEG-NH-DBCO, mol wt 10K.

FIG. 43 is an illustration of Scheme 4 for synthesis of 4-arm PEG-NH-(PEG)4-DBCO.

FIG. 44 is an illustration of Scheme 5 for synthesis of click reactive co-polymer of methacryloyloxyphosphocholine-allylamine containing click reactive DBCO groups with PEG linker.

FIG. 45 is an illustration of Scheme 6 for synthesis of co-polymer of methacryloyloxyphosphocholine-allylamine containing click reactive azide groups with PEG linker.

FIG. 46 is an illustration of Scheme 7 for synthesis of click reactive co-polymer of methacryloyloxyphosphocholine-allylamine containing click reactive DBCO groups with hydrophobic chain (C6) linker.

FIG. 47 is an illustration of Scheme 8 for synthesis of click reactive co-polymer of methacryloyloxyphosphocholine-allylamine containing click reactive DBCO groups with fluorescein tag.

FIG. 48 is an illustration of Scheme 9, illustrating two conformal coating methods of two layer system and 3 three layer system provided by the invention.

FIG. 49 is an illustration of scheme 10 for continuous addition method of conformal coating.

DETAILED DESCRIPTION

Figure 1:
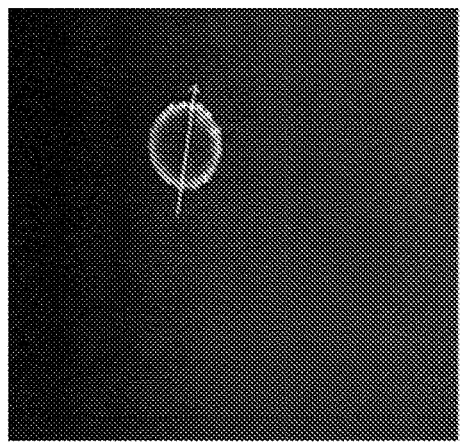
FIG. 1 is a confocal micrograph of coated polystyrene (PS) particles in sucrose medium; 4-armPEGNH2/4-arm PEGNHS.

The invention is based, at least in part, on Applicants' discovery of conformal coatings of biological surfaces that are ultra thin and semi-permeable, highly reproducible and scalable, and that do not have any significant damage (structural changes) or modification (including loss/impairment of function) of the biological surface (e.g., cell) as well as methods of making these conformally coated biological surfaces under a wide range of physiological conditions. Individually, these are the "compositions provided by the invention" (or "biological surfaces provided by the invention") and "methods provided by the invention" and collectively will be referred to as "compositions and methods provided by the invention", and the like. The compositions and methods provided by the invention advantageously overcome difficulties and limitations of exiting methods and compositions, such as damage to biological surfaces/poor biocompatibility, reproducibility, scalability, and thickness, permeability, or uniformity. See, for example, Tomei et al. Proceedings of the National Academy of Sciences (2014) 111(29), 10514-10519; L. H. Granicka et al., (2011), Artificial Cells, Blood Substitutes and Biotechnology (2011) 39: 274-280; Blasi et al., International Journal of Pharmaceutics (2013) 440, 141-147; Hubbell and Tomei, US2014/0147483 A1; Garcia et al., US2015/0071997 A1; Sang Van, et al., U.S. Pat. No. 8,216,558 B2; Chaikof, et al. U.S. Pat. No. 7,824,672 B2; Michael H. May, 1998, Ph.D. thesis, University of Toronto; Angelo S. Mao et al. Nature Materials, (2017), 16, 236-243; Green et al., Materials Today (2012), 15: 60-66; Ribeiro et al., Applied Materials & Interface, (2017), 9: 12967-12974.

Accordingly, in a first aspect, the invention provides compositions comprising a biological surface having a hydrogel conformal coating. Relative to a suitable control biological surface without the conformal coating, the biological surface: i) retains function (i.e., biological function, such as, for example, insulin secretion in response to glucose), and ii) is substantially free of or has only a negligible amount of, damage or other forms of surface modification. For example, in some embodiments, less than about: 25, 20, 19, 18, 17, 16, 15, 14, 13, 12, 11, 10, 9, 8, 7, 6, 5, 4, 3, 2, 1, 0.75, 0.5, 0.25, 0.1% of disulfide bonds, amine (—NH2), carboxylic (—COOH), or hydroxyl (—OH) moieties (or a combination of 1, 2, 3, or all 4) on the biological surface are modified.

"Conformal coating" is a thin (less than 50 µm, in some embodiments, less than about: 50, 40, 30, 20, or 10 µm; e.g., less than 20 µm, e.g., between about 5 and 20 µm, or less than or about 10 µm) exogenous coating, which is substantially uniform over the surface being coated, and which allows molecular weight sieving, i.e., passage of nutrients, certain proteins and oxygen, et cetera but not antibodies or cells. As used herein, conformal coating does not encompass significant covalent linking of the biological surface to the conformal coating or otherwise covalently modifying the surface of the biological surface. Instead, conformal coating encompasses a cross linked network, such as a hydrogel, that surrounds the biological surface without a significant amount of (i.e., less than about: 10, 9, 8, 7, 6, 5, 4, 3, 2, 1, 0.75, 0.5, 0.25, 0.1%, or preferably any, i.e., below the limit of detection) cross linking to the biological surface. In certain particular embodiments, conformal coating does not encompass: photoactivation, use of radical initiators, surfactants, acid or base catalysis, oxidizing or reducing agents, or organic solvents and, preferably, can take place over a broad range of temperatures, e.g., between about: 4° C. and 37° C. and at suitable, e.g., physiological, pH conditions. In certain embodiments, the hydrogel making up the conformal coating has a net neutral charge. Generally, the conformal coatings provided by the invention (and methods of making them) do not substantially (or at all) impact functionality of the biological surface, e.g., cell. That is, biological functions (such as insulin secretion in response to glucose) of the biological surface are negligibly, if at all, impacted. Likewise, the physical structure of the biological surface, particularly its outer surface that is proximate to the conformal coating is not modified, e.g., disulfide bonds remain substantially (or completely) intact, while other reactive groups such as amine, carboxylic, and hydroxyl are substantially (or completely) unmodified. In certain particular embodiments, less than about: 25, 20, 19, 18, 17, 16, 15, 14, 13, 12, 11, 10, 9, 8, 7, 6, 5, 4, 3, 2, 1, 0.75, 0.5, 0.25, 0.1% of disulfide bonds, amine (—NH2), carboxylic (—COOH), or hydroxyl (—OH) moieties (or a combination of 1, 2, 3, or all 4) on the biological surface are modified following the application of the conformal coating. In addition, the conformal coatings provided by the invention (and methods of making them) are permeable to molecules (e.g., nutrients, oxygen, and certain secreted molecules, such as secreted protein, such as insulin) up to about: 30, 35, 40, 45, 50, 55, 60, 65, 70, kDa, or more, e.g., 75, 80, or 85 kDa, but not larger molecules, such as antibodies or cells, and thus are impermeable to molecules about: 90, 100, 110, 120, 130, 140, 150 kDa, or more.

A "biological surface" includes live cells (including bacterial, archaeal, fungal, plant, or animal cells, such as insect or mammalian cells, such as cells from primates, such as human, as well as non human primates, as well as non primate mammal cells, such as mouse, rat, porcine, ovine, bovine, canine, feline, camelidae, leporine, et cetera), where the live cells can be in the form of individual cells, cell clusters, organoids, cell spheroids, embryoid bodies, tissues, or tissue fragments, including natural tissue explants (including whole organs or organ fragments, such as kidney, pancreas, liver, or heart) or in vitro grown tissues, as well as bioartificial/hybrid organs or organ devices. In particular embodiments, the cell is a pluripotent stem cell, such as an induced pluripotent stem cell. A biological surface also encompasses artificial cells, such as proteins (such as enzymes) linked to a non-living cell, such as a liposome, hydrogel, a solid (such as a plastic, such as polystyrene, or a PLA, PGA, or combination thereof), et cetera. Biological surfaces, such as cells, are typically (although not necessarily) substantially spherical in shape. Cells (as well as cell clusters or spheroids) can have a diameter from about 5 μm to about 1 mm, e.g., about 10 μm to 1 mm, e.g., about 100 μm to about 400 μm, e.g., in some embodiments up to about 300 μm, e.g., about: 100-300 μm. In other embodiments the biological surface (cell, cell cluster, or cell spheroid) is about: 10 μm to 2 mm, 20 μm to 1 mm, 50 to 800 μm, or 100 to 500 μm.

In some embodiments, the hydrogel of the composition provided by the invention is a covalently cross linked network of multi arm polymers, such as 4-arm 5-10 kDa PEG, methacryloyloxyethyl phosphocholine co-polymer 100-200 kDa, 60-90% phosphocholine (or other zwitterionic group; including polymers based on LIPIDURE®-NH01), as well as combinations of the same.

In another aspect, the invention provides methods of conformal coating a biological surface in a hydrogel. These methods encompass providing a system comprising two aqueous layers, the first layer comprising a solution of about: 0.25% to 2% (W/V) of a suspending agent, about 1% to about 25% (W/V) of a first functionalized multi arm polymer, and the biological surface and a second layer comprising a saccharide cushion and about 1% to about 25% (W/V) of a second functionalized multi arm polymer, the functional group of the second functionalized multi arm polymer being reactive with the functional group of the first functionalized multi arm polymer under physiological conditions, and then causing the biological surface to pass into the second layer, thereby allowing the first and second functional groups to react and form a cross-linked hydrogel conformally coating the biological surface. As noted previously, the methods provided by the invention can use more than two layers, e.g., three or more layers, and can include more than one saccharide cushion. Typically, the aqueous layers are substantially free of radicals and organic solvents (e.g., less than 1.0, 0.9, 0.8, 0.7, 0.6, 0.5, 0.4, 0.3, 0.2, 0.1, 0.05% (V/V) radicals or organic solvents, or, in some embodiments, below the limit of detection).

A "suspending agent" is a chemical that increases the viscosity of an aqueous solution and includes linear, comb shaped multi-valent polymers, branched, homo and block polymers. Exemplary suspending agents include polyethylene glycol (PEG), including high molecular weight PEG (also known as polyethylene oxide, PEO), as well as PVA (polyvinyl alcohol), PVP (polyvinylpyrrolidone), and HPMC (hydroxypropyl methylcellulose). The suspending agent may be either linear or branched. The suspending agent is present at about: 0.05% to 2.0%, e.g., about: 0.1% to 2.0%, or about: 0.25% to 2.0%, or about 1%, e.g., 0.5% to 1.5%. In certain embodiments, the suspending agent has a molecular weight of about 1 MDa (megadalton) to about 10 MDa, e.g., about 1 MDa to about 8 MDa. In particular embodiments, the suspending agent is PEO with a molecular weight of between about: 1 MDa to 10 MDa, e.g., 1 MDa to 8 MDa, e.g., at the above concentrations. As will be appreciated by the skilled artisan, other suspending agents can be used so as to achieve properties similar to results described herein for high molecular weight PEO, e.g., about 1% of about 1 MDa to about 8 MDa. The suspending agent can be dissolved in a variety of aqueous solutions, such as, for example, saline, e.g., 0.9% saline. In some embodiments, a suspending agent is present in the first layer only, while in other embodiments a suspending agent is present in both the first and second layers. In some embodiments where a suspending agent is present in both layers, the suspending agent in the first layer is the same as the suspending agent in the second layer, while in other embodiments, the suspending agents may be different.

A "saccharide cushion" is a 1%-15% (W/V) solution of mono, di, tri, oligo, or polysaccharides (e.g., sucrose, glucose, trehalose, mannitol, dextrose, fructose, lactose, maltose, or a combination thereof) that increases the density of a solution and facilitates a layering of aqueous solutions as described herein. In certain embodiments, the saccharide is about 5% to about 15%, e.g., about 7.5% to about 12.5%, e.g., about 10% of the solution. In certain particular embodiments, the saccharide is sucrose. Other saccharide cushions can be used, based on, for example, achieving a similar density to sucrose at the particular concentrations exemplified herein. In some embodiments, the methods provided by the invention use two layers, or more, such as three layers, or more still.

A "functionalized multi arm polymer" is a multi arm polymer with three or more (e.g., 3 to 12, more particularly, 4 or 8) arms that have functional groups at the distal ends of the arms. The arms may, in some embodiments, radiate from a central core (such as multi-arm PEG) or, in other embodiments, come off of at different points along the length of a central axis polymer (as in a comb-shaped polymer, such as a co-polymer), in which case the multi-arm polymer may have more than 4 arms, e.g., about: 20, 25, 30, 35, 45, 50, 75, 100, 150, 200, 300, 400, 500, 600, 700, 800, 900 arms or more, and the co-polymer contains a substantially uniform distribution of the different polymers along its axis for its full size/mass, e.g., of about: 10 kDa-1 MDa, 20 kDa-800 kDa, 50-500 kDa, e.g., about: 100-400 kDa, 100-300 kDa, 200-350 kDa, 200-300 kDa, or about 300 kDa, e.g., about 275-325 kDa. The functionalized multi arm polymer has functional groups at the distal ends of the arms, e.g., at distal ends of two or more of the arms, e.g., from two, up to n arms, where n is the number of arms on a multi-arm polymer, e.g., where n=4, there may be 2, 3, or all 4 arms have a functional group at their distal ends. In some embodiments, about 5, 10, 15, 20, 25, 30, 35, 40, 45, 50, 55, 60, 65, 70, 75, 80, 85, 90, 95% of all arms have a functional group at their distal ends, e.g., about 5-15% of all arms have a functional group at their distal ends, for example, where the multi-arm polymer is a large comb-shaped polymer. The functionalized multi arm polymer is present in solutions at about 1% to about 25% (W/V), e.g., about 2.5% to about 20%, more particularly about 8% to about 12%, or about 10%. In some embodiments a functionalized multi arm polymer is present at about 5% to about 10%. In other particular embodiments, the multi arm polymer is present in solutions at about 2.5% to 7.5%, e.g., about 4% to about 6% or about 5%.

In certain embodiments, the functionalized multi arm polymer is PEG, e.g., with a total molecular weight of about: 5-40, 5-30, 10-20, 8-12, or 10 kDa, e.g., 4 or 8 arm PEG with a molecular weight of about: 5-40, 5-30, 10-20, 8-12, or 10 kDa, e.g., at about: 5% or 10% W/V.

In other embodiments, the functionalized multi arm polymer is a linear co-polymer with methacryloyloxyethyl or other backbone (such as polyvinyl or polyamide), such as a co-polymer comprising phosphocholine or other zwitterionic group, e.g., where about: 40, 45, 50, 55, 60, 65, 70, 75, 80, 85, 90, or 95% of the co-polymer arms include the zwitterionic group, e.g., 60-90%, 70-90%, 75-85%, or about 80% of arms, referenced, for simplicity, as percentage zwitterionic group-containing arm in the polymer, such as percentage phosphocholine, e.g., 60-90% phosphocholine. In these embodiments, the remaining 60, 55, 50, 45, 40, 35, 30, 25, 20, 15, 10, or 5% of the co-polymer arms contain a functional group, such as allylamine (such as the co-polymer sold under the name LIPIDURE®-NH01), or derivatives, such as functionalized arms in which the $NH_2$ groups of allylamine units of the co-polymer are appended with click functional groups, such as DBCO or azide (optionally with intervening linkers, such as PEG, where the linker can be about: 2-80, 3-60, 3-50, 5-40, 10-40, 15-40, 20-40, 25-40, 30-40, 35-40, or 38 atoms (such as C, N, O, P, S, or a combination thereof) in length). In some embodiments, the percentage of the functional groups (e.g., such as allylamine) that are converted to functionalized derivatives (e.g., with an appended click-functional group, with optional intervening linker) is about: 25, 30, 35, 40, 45, 50, 55, 60, 65, 70, 75%, or more, e.g., about: 25-75%, 40-60%, 45-55%, or 50%. Thus, for example, in embodiments where 60-90% of a co-polymer is zwitterionic arms, 40-10% of the arms of the co-polymer are available for conversion to have click functional groups, of which, in some embodiments, about 50% are appended with click functional groups, i.e., 20-5% of the total number of arms have appended click functional groups. Accordingly, in certain embodiments, about: 50, 60, 80, 80, 90, 100, 110, 120, 130, 140, 150, 160, 170, 180, 190, 200 arms, or more, e.g., about: 70-150 or 80-90, or about 85 arms in a comb-shaped functionalized multi arm polymer have an appended click functional group.

In other embodiments, the functionalized multi arm polymer is methacryloyloxyethyl phosphocholine (MPC; e.g., in some embodiments, functionalized with DBCO, such as lysine-DBCO, in other embodiments with allylamine co-polymer), e.g., in more particular embodiments the functionalized multi arm polymer in the first layer is MPC (e.g., MPC-lysine-DBCO), and the functionalized multi arm polymer in the second layer is PEG, e.g., 4 or 8 arm PEG (e.g., PEG-azide). In other embodiments, the functionalized linear co-polymer is methacryloyloxyethyl phosphocholine-allylamine (e.g., LIPIDURE®-NH01) functionalized the $NH_2$ groups of allylamine units of co-polymer with click functional DBCO as the first polymer; and the functionalized linear co-polymer methacryloyloxyethyl phosphocholine-allylamine (e.g., LIPIDURE®-NH01) functionalized the amine groups of allylamine units of co-polymer with click functional azide groups as the second polymer. In some embodiments, the co-polymer of methacryloyloxyethyl phosphocholine-allylamine is about: 80:20 mole ratio; 50:50 mole ratio; 20:80 mole ratio.

A "multi arm polymer" as used herein encompasses functionalized multi arm polymer, as well as polymers that are substantially identical, but lack functional groups, e.g., a hydrogel made up of cross-linked (i.e., reacted) functionalized multi arm polymers that no longer have reactive functional groups at the distal ends of the polymer arms (i.e., less than about: 10, 9, 8, 7, 6, 5, 4, 3, 2, 1, 0.75, 0.5, 0.25, 0.1% of unreacted functional groups remain). In certain embodiments, the first functionalized multi arm polymer is the same as the second functionalized multi arm polymer, except that the two functionalized multi arm polymers have complementary (reactive) functional groups, such as DBCO and azide functionalized methacryloyloxyethyl co-polymers, respectively or DBCO and azide functionalized multi-arm PEGs, respectfully. In other embodiments, the first functionalized multi arm polymer is different from the second functionalized multi arm polymer, e.g., DBCO or azide functionalized methacryloyloxyethyl co-polymer with azide or DBCO functionalized multi-arm PEG.

Functional groups on the functionalized multi arm polymers useful in the methods provided by the invention are reactive groups that facilitate efficient cross linking between the first functionalized multi arm polymer and second functionalized multi arm polymer to form a stable hydrogel. A variety of suitable chemistries will be recognized by the skilled artisan as being suitable for this purpose. Exemplary chemistries include NHS/activated esters and, in particular embodiments, click functional groups.

A "click functional" (sometimes referenced as click reactive) group is a chemical moiety suitable for click chemistry, i.e., single pot reactions that are specific, proceed rapidly (high thermodynamic driving force) under biological conditions, are not disturbed by water, and do not generate significant toxic or offensive byproducts. Suitable click functional groups undergo chemistry reactions such as cycloadditions such as 1,2-dipolar cycloadditions and hetero-Diels alder cycloadditions; nucleophilic ring openings of strained heterocyclic electrophiles such as aziridines, epoxides, cyclic sulfates, episulfonium, et cetera; non-aldol carbonyl chemistry to form ureas, thiorureas, hydrozones, oxime ethers, amides and aromatic heterocycles; and additions to carbon-carbon multiple bonds, such as epoxidations, aziridinations, dihydroxylations, sulfenyl halide additions, nitrosyl additions, and Michael additions. In certain embodiments, click chemistry reaction pairs (i.e., click functional groups on the first and second functionalized multi-arm polymer) include azide-DBCO (dibenzocyclooctyne) (resulting in a triazole linkage), thiol-norborene (Michael addition), and tetrazine-norborene (pyrazo linkage). In certain particular embodiments, click functional groups useful in the present invention include azide and DBCO.

In certain embodiments of the methods provided by the invention, the first functionalized multi arm polymer is 4-arm 5-10 kDa PEG. In more particular embodiments, the functional group of the first functionalized multi arm polymer is a click functional group, such as DBCO or azide. In other particular embodiments of the methods provided by the invention, the first functionalized multi arm polymer is a methacryloyloxyethyl phosphocholine co-polymer 100-200 kDa, 60-90% phosphocholine. In more particular embodiments, the functional group of the first functionalized multi arm polymer is a click functional group, such as DBCO or azide.

In some embodiments of the methods provided by the invention, the second functionalized multi arm polymer is 4-arm 5-10 kDa PEG. In more particular embodiments, the functional group of the second functionalized multi arm polymer is a click functional group, such as azide or DBCO. In other particular embodiments of the methods provided by the invention, the second functionalized multi arm polymer is a methacryloyloxyethyl phosphocholine co-polymer that is 100-200 kDa and 60-90% phosphocholine. In more particular embodiments, the functional group of the second functionalized multi arm polymer is a click functional group, such as azide or DBCO.

In some embodiments of the methods provided by the invention, the suspending agent is PEO with a molecular weight of between about 1-8 MDa that is present at about 1%.

In certain embodiments of the methods provided by the invention, the biological surface is caused to pass into the second layer by centrifugation.

In certain embodiments of the methods provided by the invention, the biological surface is continuously added drop by drop under centrifugation to the bottom layer.

In certain embodiments the centrifugation vial is designed suitable for the continuous addition of biological surface by inserting tapered side arm with an orifice small enough to allow the mixture travel under centrifugal force drop by drop.

Thus, in another aspect, the invention also provides methods of conformal coating a biological surface in a hydrogel by providing a system comprising two aqueous layers separated by an intervening layer (such as a gaseous layer), the first layer comprising a solution of about: 0.25% to 2% (W/V) of a suspending agent, about 1% to about 25% (W/V) of a first functionalized multi arm polymer, and the biological surface and a second layer comprising a solution of about: 0.25% to 2% (W/V) of a suspending agent, saccharide cushion, and about 1% to about 25% (W/V) of a second functionalized multi arm polymer, the functional group of the second functionalized multi arm polymer being reactive with the functional group of the first functionalized multi arm polymer under physiological conditions, and causing the biological surface to pass into the second layer, thereby allowing the first and second functional groups to react and form a cross-linked hydrogel conformally coating the biological surface, where the first functionalized multi arm polymer is a linear methacryloyloxyethyl phosphocholine co-polymer.

In certain embodiments of these methods the first layer is continuously added to the second layer. In some embodiments, the second layer is within a container suitable for the addition of the first layer through a tapered side arm with an orifice dimensioned to allow the mixture travel under centrifugal force. One illustration of such embodiments is a drop by drop addition, as shown in FIG. 49, this way the biological surface enters the layer of $2^{nd}$ functionalized polymer in saccharide solution containing suspending agent. This process avoids the trapping of cells at the interface and provide high yield of coated biological surfaces. In certain embodiments, the substantially continuous addition of the first layer to the second layer results in a yield of at least 50, 60, 70, 75, 80, 85, 90, 95% or more of conformally coated biological surface relative to the amount of starting biological surface, e.g., the continuous addition methods with cells, such as islets, results in at least 50, 60, 70, 75, 80, 85, 90, 95% or more of the starting (uncoated) cells ending as fully coated cells. In certain embodiments, the upper orifice diameter is 200 micrometer to 5000 micrometer; the lower orifice diameter is 5 micrometer to 1000 micrometer, preferably 10 micrometer 500 micrometer.

In particular embodiments for the compositions and methods provided by the invention, the thickness of the conformal coating is less than about 20 μm, e.g., is about: 10-20 μm, 5-10 μm, 7.5-12.5 μm, or 10 μm.

In certain embodiments for the compositions and methods provided by the invention, the biological surface is a living cell (e.g., animal, plant, bacteria, yeast cell) or cell cluster. In particular embodiments, the living cell is an animal cell. In more particular embodiments, the animal cell is a mammalian cell. In yet more particular embodiments, the mammalian cell is a human cell. In other particular embodiments where the biological surface is a cell, the cell is an insulin-producing cell. In some particular embodiments where the biological surface is a cell, the cell is a pluripotent stem cell, such as an induced pluripotent stem cell (iPSC), such as a mammalian iPSC, such as a human iPSC.

In particular embodiments of the compositions and methods provided by the invention, where the cell is an insulin-producing cell, upon stimulation with glucose at about 2 mM to about 20 mM, relative to a suitable control cell not subjected to the conformal coating, the cell secretes insulin with kinetics and/or at a concentration that is substantially similar to the suitable control cell, e.g., within about: 1, 2, 3, 4, 5, 6, 7, 8, 9, 10, 15, 20, 25, or 30 minutes to peak insulin secretion from the control cell and/or within about: 5, 10, 15, 20, 25, 30, 40, or 50% of the concentration of insulin from the control cell (e.g., at 10, 20, 60, 90, or 120 minutes).

In a related aspect, the invention provides biological surfaces having a hydrogel conformal coating, prepared by any of the methods provided by the invention.

In another aspect, the invention provides compositions comprising the biological surfaces provided by the invention and one or more pharmaceutically acceptable diluents or excipients, e.g., for use in treating a mammalian subject by administering a therapeutically effective amount of a composition provided by the invention.

In another aspect, the invention provides methods of treating a subject in need thereof (e.g., lacking or deficient in a certain biological function provided by a composition provided by the invention) comprising providing a composition provided by the invention that ameliorates the need of the subject. In certain embodiments, the subject is a human, such as an adult or pediatric subject, e.g., with insulin-dependent diabetes. The compositions provided by the invention used in such methods can be applied directly to the subject (e.g., by injection or implantation, in which case the compositions provided by the invention are provided in a syringe suitable for administration to a mammalian subject, such as a human) or may be provided in a biocompatible container that is implanted in the subject, e.g., the composition provided by the invention is disposed within a biocompatible container that restricts its movement within the subject, but that is semi-permeable and permits diffusion of, e.g., nutrients, oxygen, and therapeutic agents.

EXEMPLIFICATION

Overview

Ultra-thin conformal coating was achieved utilizing multi-arm click-reactive hydrophilic polymers that were capable of reacting specifically one polymer to another at neutral pH in aqueous isotonic system at desired temperature suitable to specific living cells. First, the method was developed using polystyrene particles (100 to 125 micron range) as model for cell spheroids, using activated N-hydroxy succinimide (NHS) ester approach that consists of a 4-arm PEG-NHS and 4-arm PEG-NH2. In order to achieve this, initially 4-arm PEG-NH2 with FITC label was layered on the particle surface, which was found to be an important step in the process. This was accomplished by mixing the particles with 5% 4-arm PEG-NH2 spiked with 4-arm-PEG-(NH2)3-FITC (1% solution). The mixture was vacuum dried at 30° C. for 6 hours. The resultant powder was suspended in 60% sucrose solution that contains 4-arm PEG-NHS (5%). The mixture was vortexed and washed with PBS buffer to remove excess sucrose, un-reacted PEG and excess fluorescent PEG polymer and salts. The particles were collected and visualized under confocal microscope in fluorescence field. The microscopic images confirmed that ultra-thin coat was formed uniformly on the particle surface with a thickness of 5 to 10 micron range, FIG. 1. Thus the concept of conformal coating using two-reactive polymers in aqueous system has been proved, however the working conditions and reagents such tetra PEG-NH2, tetra-PEG-NHS esters, and vacuum drying and use of hypertonic sucrose 60% solution are not desirable for living cells.

Figure 2:
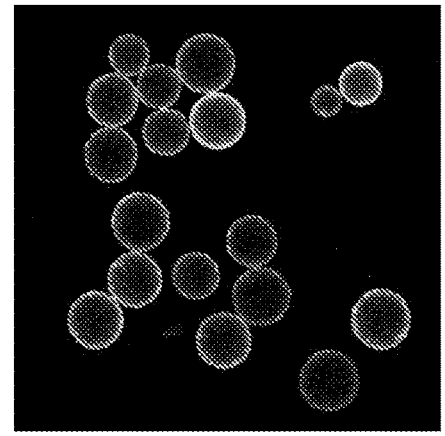
FIG. 2 is a confocal micrograph of coated PS particles, PEO (8 million mol wt), 4-armPEG-NHS/4-arm PEG-NH2.
Figure 3:
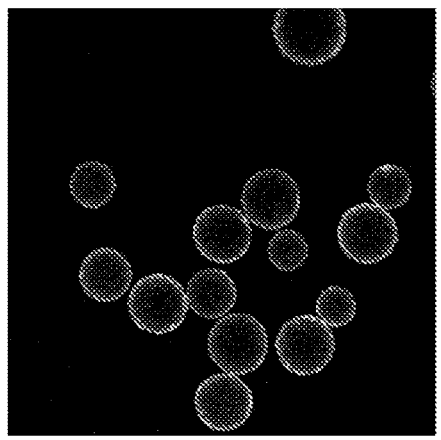
FIG. 3 is a confocal micrograph of coated PS particle, PEO (4 million mol wt), 4-armPEG-NHS/4-arm PEG-NH2.
Figure 4:
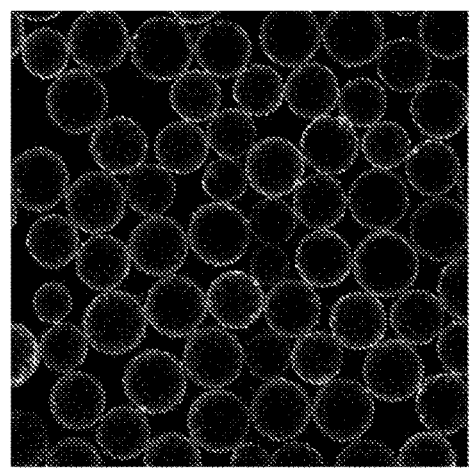
FIG. 4 is a confocal micrograph of coated PS particle, PEO (1 million mol wt), 4-armPEG-NHS/4-arm PEG-NH2.
Figure 23:
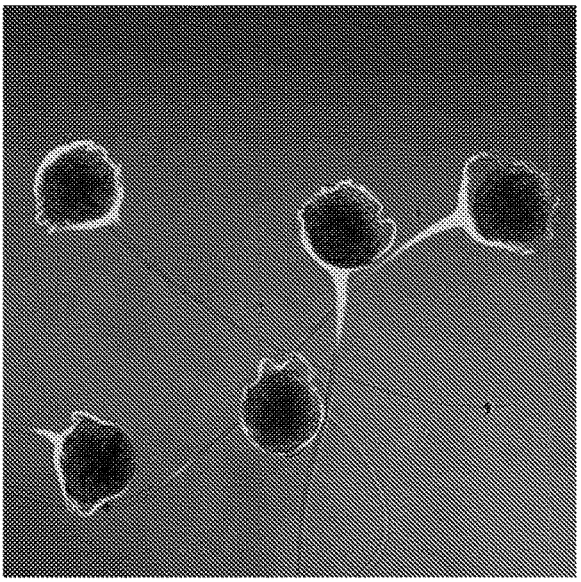
Figure 24:
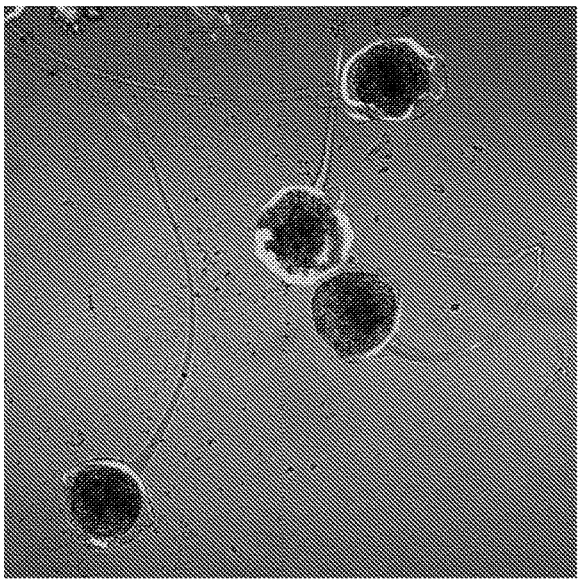
Figure 25:
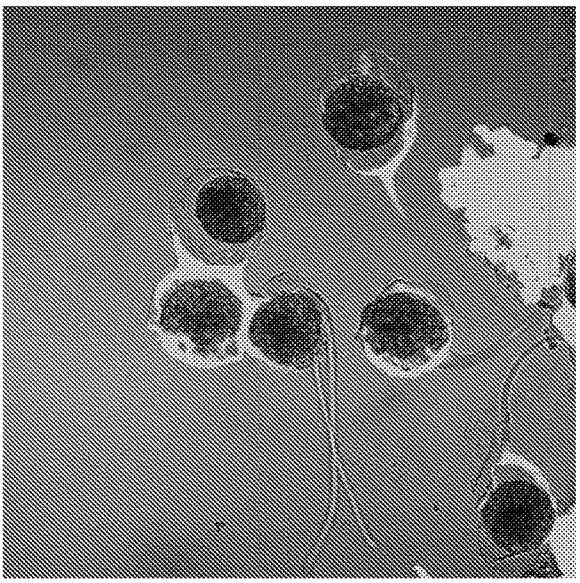
Figure 26:
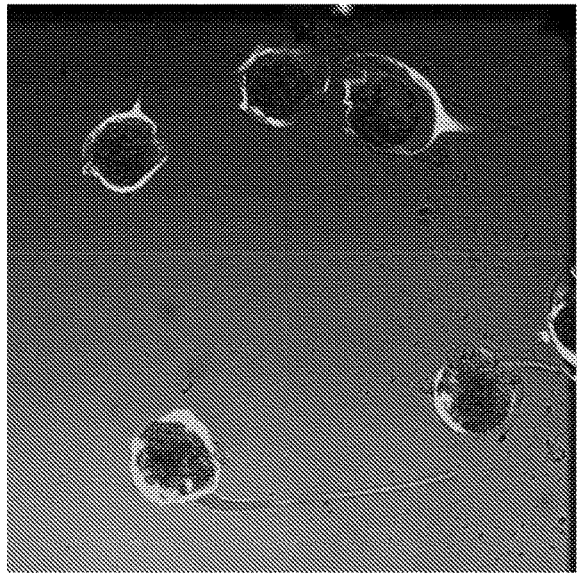
Figure 27:
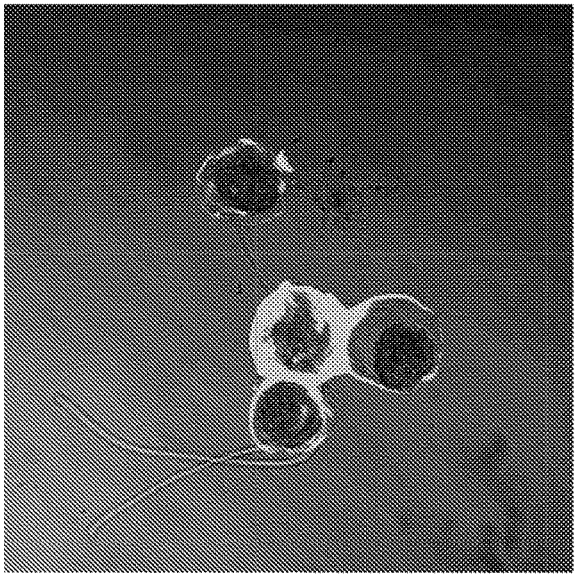
Figure 28:
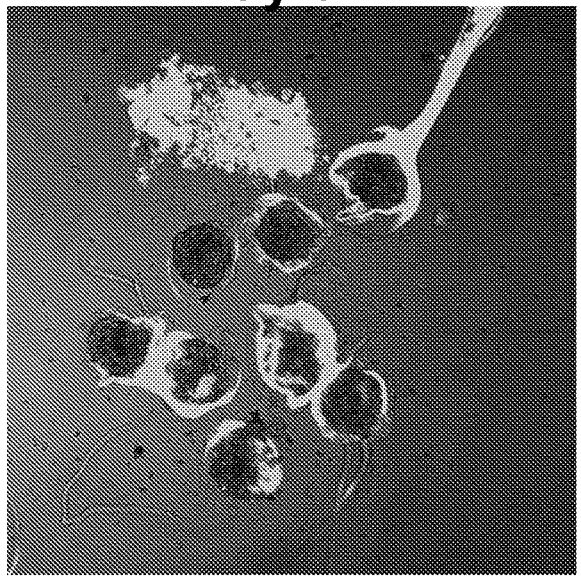

Several suspending mediums were investigated to replace 60% sucrose solution and it was found that high mol wt PEO 1 million to 8 million of 1% solution were useful to replace the hyper tonic sucrose solution as suspending media. Also, it was evaluated to replace the vacuum drying step with density gradient approach of mixing the first polymers with the particles in high mol wt PEO solution. This is considered as one layer. The long polymer chains of high mol wt PEO force the short chains of 4-arm PEG-NH2 to be retained temporarily on the particle surface. As these particles travel to the bottom layer as shown in scheme 5 (FIG. 23), which has 4-arm PEG-NHS in isotonic sucrose solution the PEG-NHS molecule penetrates through the PEO chains and react quickly with 4-arm PEG-NH2 thus form covalently linked hydrogel network on the particle surface uniformly, FIGS. 2, 3, and 4. This confirms that the hypertonic sucrose (60%) solution could be replaced with 1% PEO solution and the vacuum drying could be eliminated by using density gradient method. Even though this approach worked and was reproducible, still it was not ideal for living cells as the activated ester could react with cell surface proteins, hence it was desirable to replace the activated esters by more favorable polymerization chemistry. It was believed that click-chemistry would be a suitable chemical approach for living cells.

Figure 5:
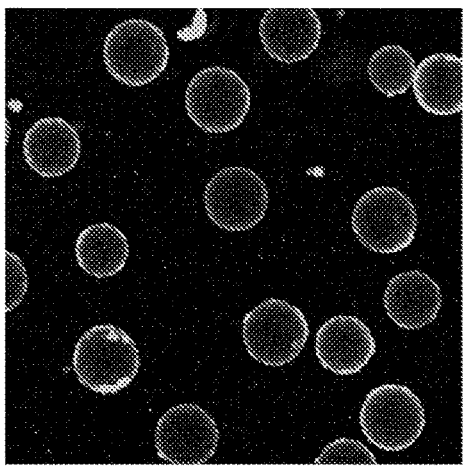
FIG. 5 is a confocal micrograph of coated PS particle, PEO (1 million mol wt), 4-armPEG-N3/4-arm PEG-DBCO.
Figure 6:
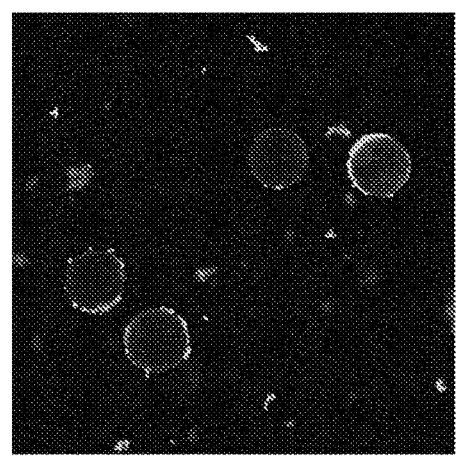
FIG. 6 is a confocal micrograph of coated PS particle, PEO (8 million mol wt), 4-armPEG-N3/4-arm PEG-DBCO.
Figure 7:
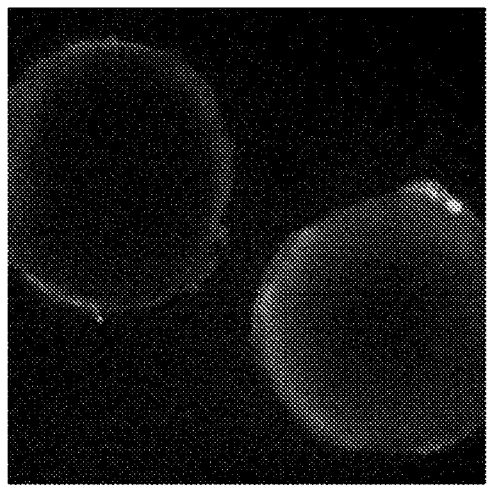
FIG. 7 is a confocal micrograph of coated HCT116 spheroid 500 cells, PEO (1 million mol wt), 4-armPEG-N3/4-arm PEG-DBCO.
Figure 8:
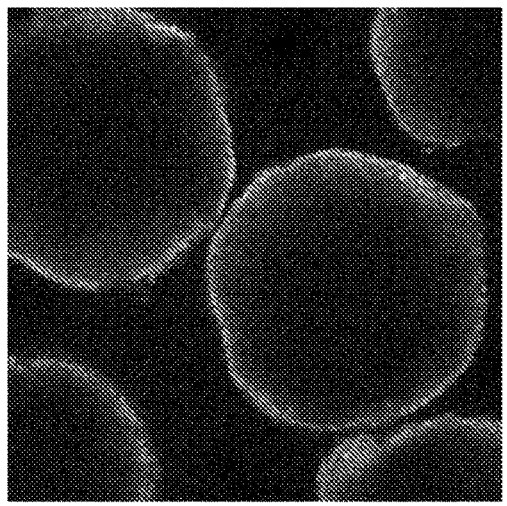
FIG. 8 is a confocal micrograph of coated HCT116 spheroid 500 cells, PEO (4 million mol wt), 4-armPEG-N3/4-arm PEG-DBCO.
Figure 9:
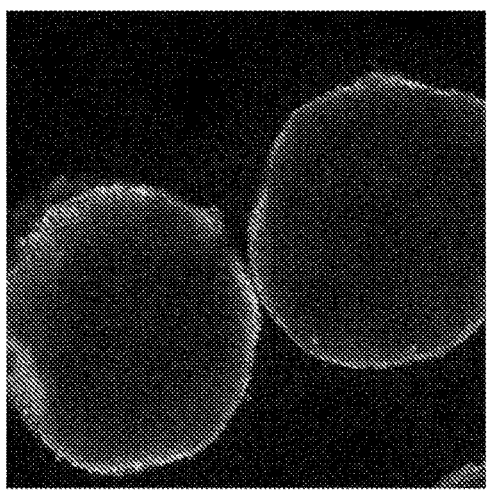
FIG. 9 is a confocal micrograph of coated HCT116 spheroid 500 cells, PEO (8 million mol wt), 4-arm PEG-N3/4-arm PEG-DBCO.
Figure 13:
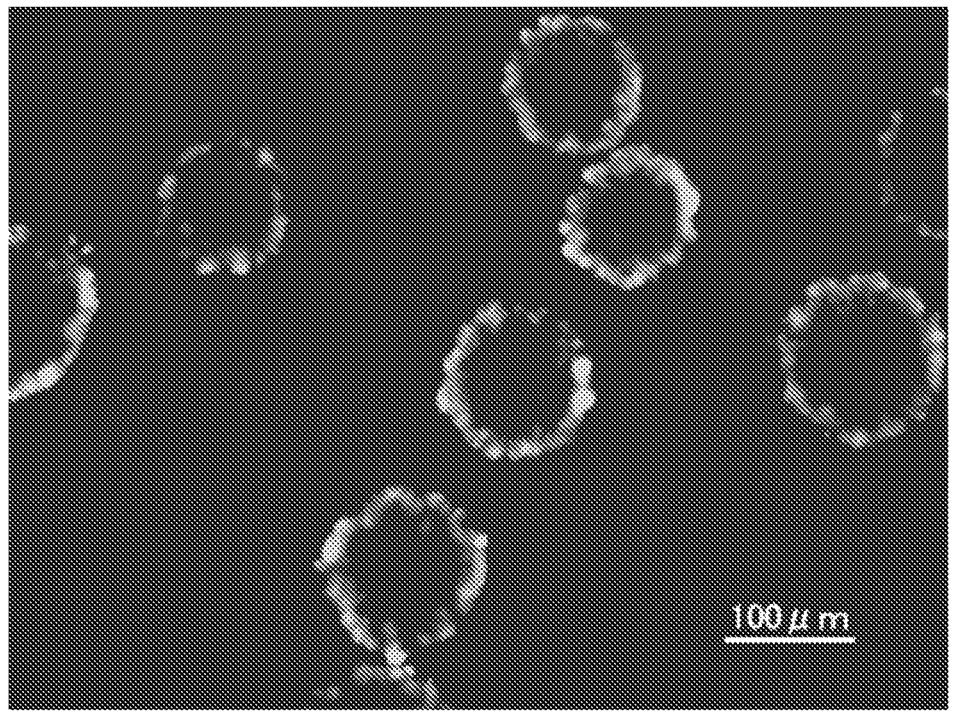
FIG. 13 is a micrograph of coated rat insulinoma cell spheroids under conventional fluorescence microscope.
Figure 14:
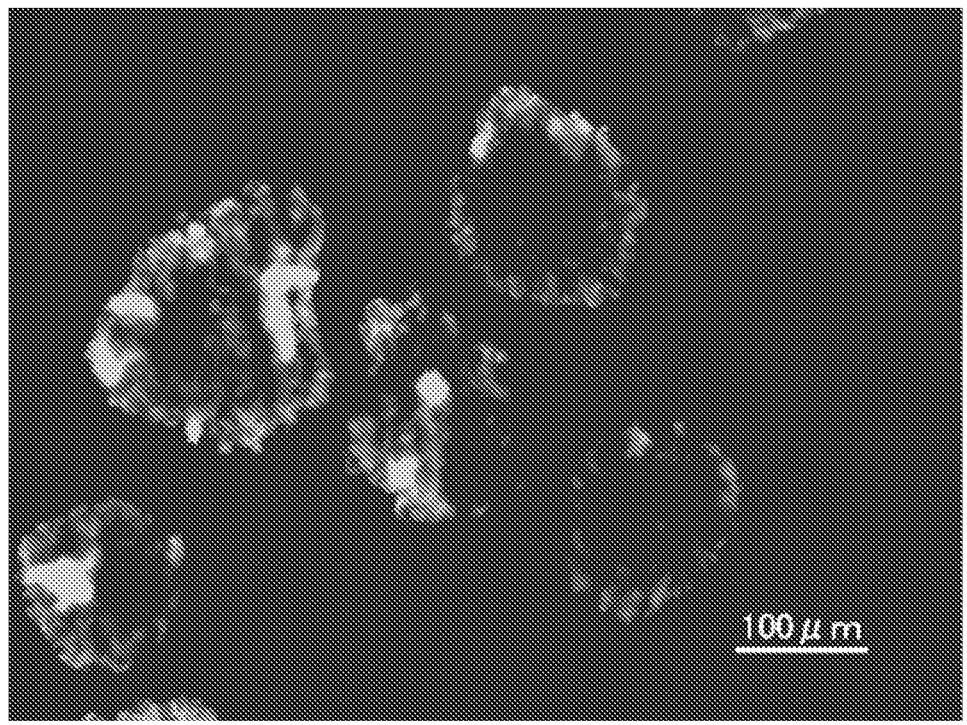
FIG. 14 is a micrograph of coated rat pancreatic islets under conventional fluorescence microscope.

Click reactive multi-arm PEGs such 4-arm PEG-DBCO (dibenzocyclooctyne) and 4-arm PEG-azide were considered to replace of 4-arm PEG-NH2 and 4-arm PEG-NHS esters. The click-reaction takes place at neutral conditions which is desirable for living cells. Several high mol wt PEO 1 million to 8 million of various concentration solutions were screened using density gradient approach as described above. This involved layering the first polymer on the particle surface in high mol wt PEO solution. The long polymer chains of high mol wt PEO forced the short chain 4-arm PEG-DBCO to retain temporarily on the particle surface. As these particles traveled to the bottom layer which had 4-arm PEG-azide in 5% sucrose solution, PEG-azide molecule penetrated through the PEO chains and reacted quickly with 4-arm PEG-DBCO, thus formed covalently linked hydrogel network on the particle surface, FIGS. 5 and 6. These conditions were found to be ideal for the conformal coating of living cells. Prior to applying this to living cells, the click-chemistry approach was applied to polystyrene (PS) particles and it was found working without any issues FIGS. 5 and 6. Then these methods were applied to successfully to HCT116 cell spheroids (FIG. 7 to 9), insulinoma cell spheroids (FIG. 13) and freshly isolated rat pancreatic islets (FIG. 14).

HCT cell spheroids (hct116 cell line), insulinoma spheroids (human origin) or rat pancreatic islets were mixed with a solution of 4-arm PEG-DBCO 5% spiked with 1% solution of 4-arm PEG-(DBCO)3-FITC in PEO (1 million to 8 million) 1% solution. The mixture was layered on the bed of 4-arm PEG-azide in 10% sucrose solution. Long polymer chains of high mol wt PEO may push the short chain 4-arm PEG-DBCO towards the cell surface as they travel into the sucrose layer where the 4-arm PEG azide penetrates and react quickly with 4-arm PEG-DBCO to form covalent links between the two polymers, thus forms a thin coat uniformly around the cell spheroid or islet. The travel rate is controlled by centrifugation force and the viscosity of PEO solution. The coat thickness can be influenced by particle travel rate, concentration of the two click-reactive PEG polymers, suspending agent polymer mol wt and viscosity. The coated spheroids settled at the bottom, which were collected by removing the supernatant liquid. The coated spheroids were washed with buffer/plasma to remove the additives such as PEO, sucrose, salts and un-reactive PEGs by centrifugation at 4° C. The coated cell spheroids and pancreatic islets were visualized using confocal microscope as well as conventional fluorescence microscope under fluorescence field. Ultra-thin coat was formed uniformly around the spheroids in the range of 5 to 10 microns thickness. The cells were survived under these conditions and exhibited their full functionality after coating.

Figure 11:
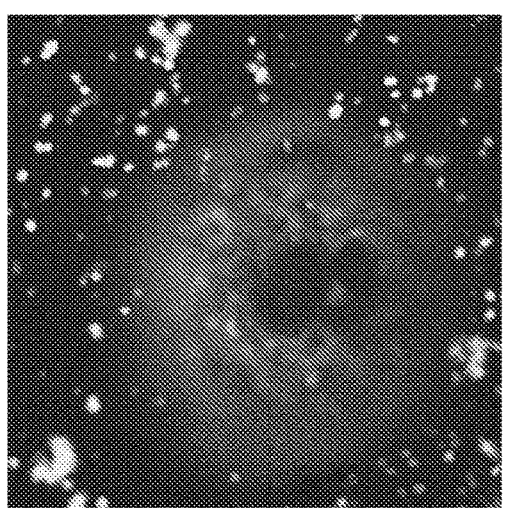
FIG. 11 is a confocal micrograph of naked HCT116 1000 cells/spheroid; cell viability stain on Day 3.
Figure 12:
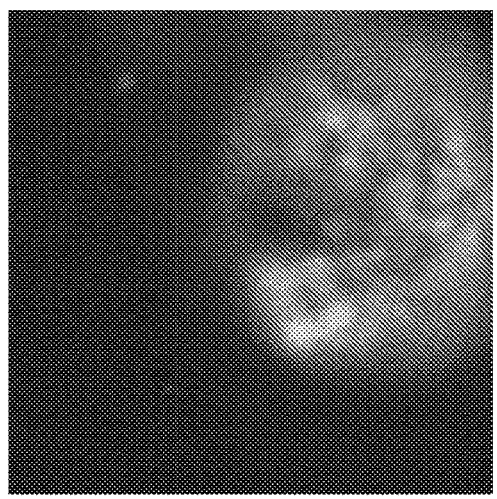
FIG. 12 is a confocal micrograph of coated HCT116 1000 cells/spheroid; PEO 8 million 4-arm PEG-DBCO: 4-arm PEGazide; cell viability stain on Day 3.

The Live/Dead cells were investigated in the coated HCT116 spheroids and the corresponding naked spheroids using calcian/ethidium homodimer-1 (Ethd-1) at day 3. It was found that coated spheroids have high percentage of live cells (appear in green color, FIG. 12), compared to the naked spheroids which has significantly high number of dead cells (red color, FIG. 11). This data indicates that the conformal coat provided stability to the cells, thus they survived for longer time compared to the naked cells in vitro.

The insulin secretion and release kinetics of conformal coated insulinoma spheroids and rat pancreatic islets were compared correspondingly with barium/alginate microencapsulated and uncoated spheroids/islets.

Figure 15:
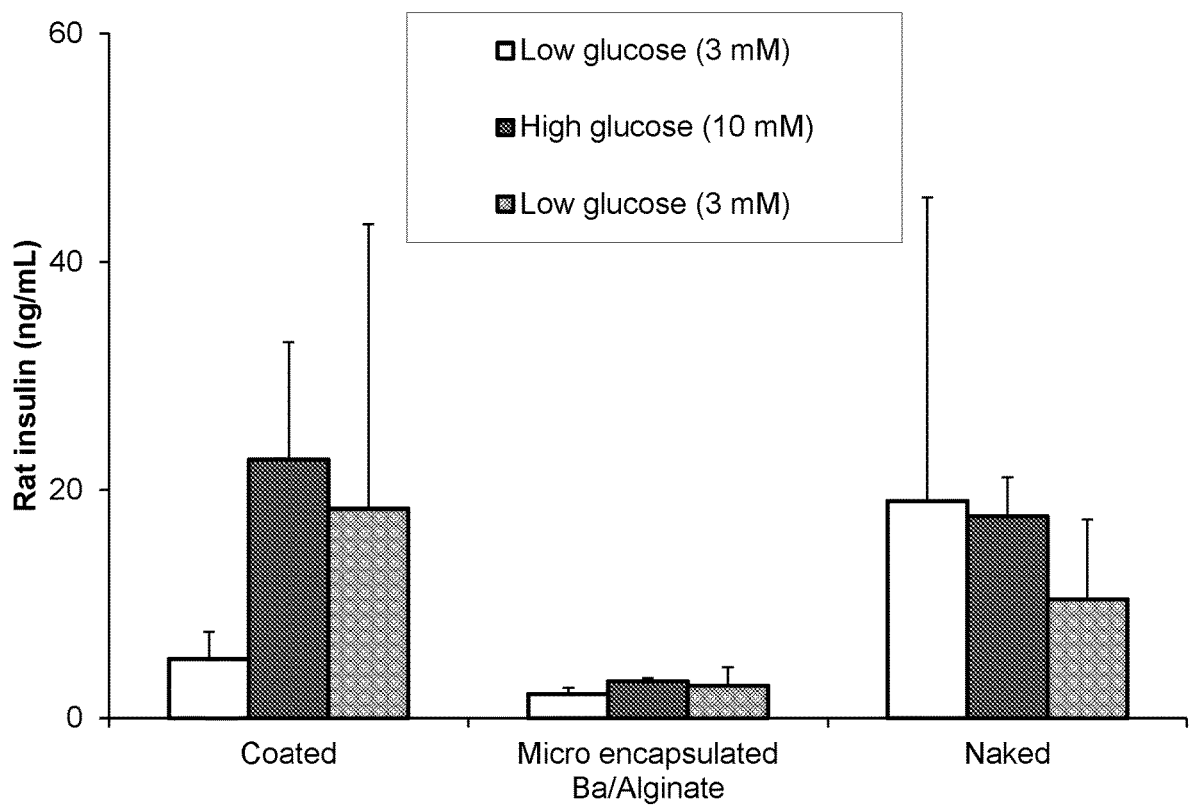
FIG. 15 is a bar graph summarizing insulin secretion study with rat insulinoma cell spheroids providing a comparison of insulin secretion response to glucose for: conformal coated, naked, and microencapsulated rat insulinoma cell spheroids formulations.
Figure 17:
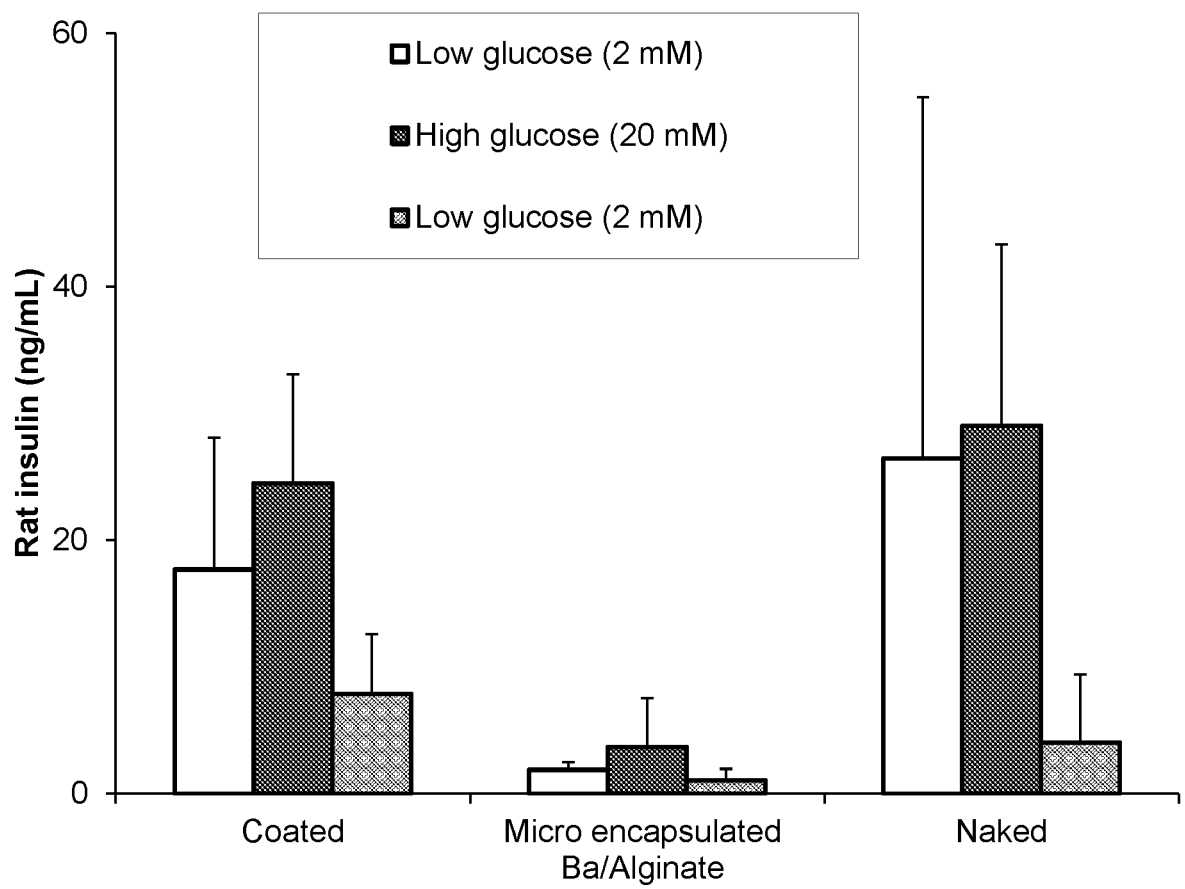
FIG. 17 is a bar graph summarizing an insulin secretion study with rat pancreatic islets, comparing insulin secretion response to glucose in rat pancreatic islets that were conformal coated, naked, or microencapsulated.

Conformal coated spheroids and rat pancreatic islets secreted insulin in response to glucose very well, equally to the corresponding uncoated version but better than microencapsulated formulations at low, medium and high glucose concentrations, (FIGS. 15 and 17).

Figure 16:
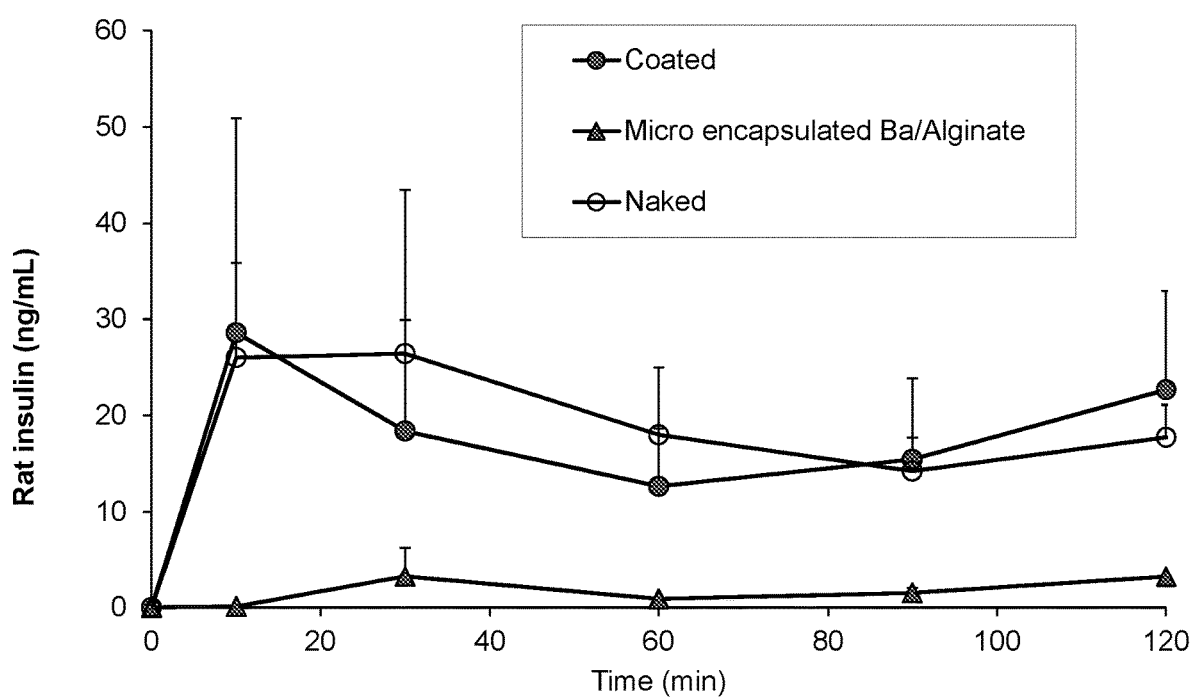
FIG. 16 is a line graph summarizing insulin secretion kinetics with rat insulinoma cell spheroids in which insulin secretion kinetics were measured in high glucose buffer, comparing conformal coated, naked, and microencapsulated rat insulinoma spheroid formulations.
Figure 18:
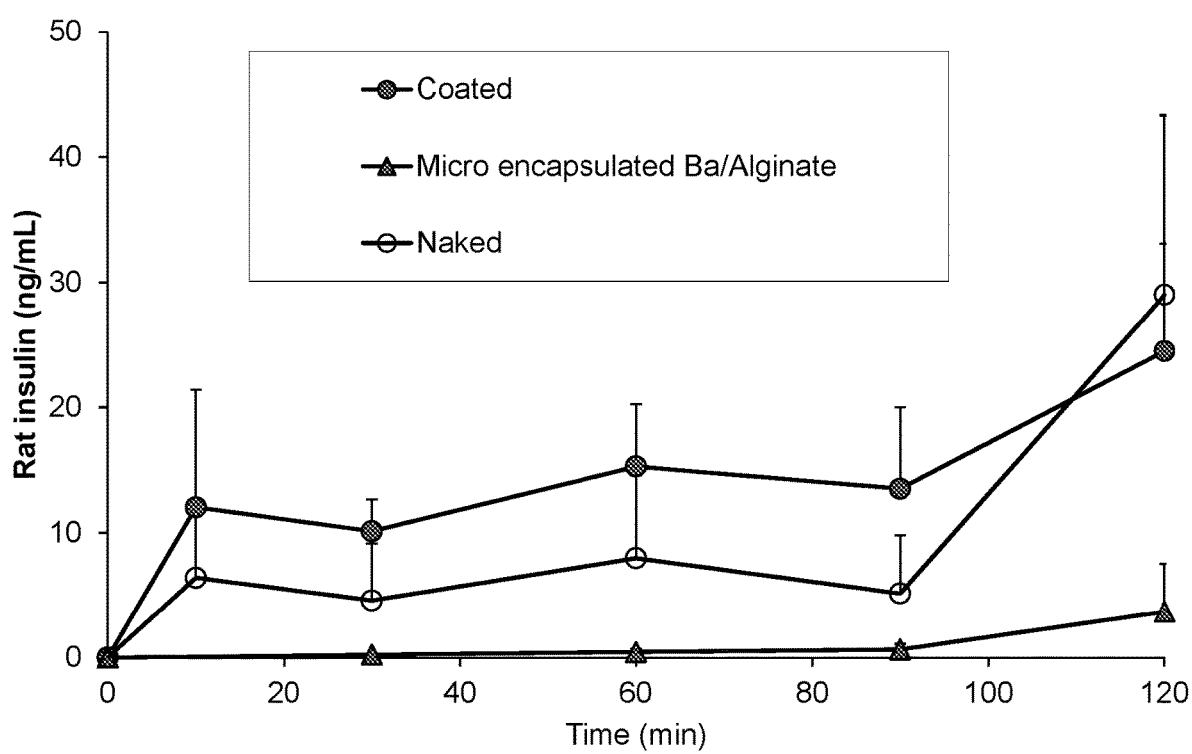
FIG. 18 is a line graph summarizing rat pancreatic islets insulin secretion kinetics in high glucose buffer, comparing conformal coated, naked, and microencapsulated rat pancreatic islet formulations.

Insulin release kinetics of conformal coated formulations was found to be better than the naked and barium/alginate micro-encapsulated formulations (FIGS. 16 and 18).

Materials and Methods:

4-arm-PEG-NHS ester mol wt 5 k, 4-arm-PEG-NHS ester mol wt 5 k and 10 k, 4-arm PEG-azide 5 k and 10 k, were purchased from JenKem technology USA. 4-arm PEG-$NH_2$ 5 k and 10 k were purchased from Creative PEG Works. DBCO reagents and solvents were purchased from Sigma-Aldrich. Polystyrene particles 106 to 125 micron size was purchased from Polysciences Inc, PA, USA. HCT 116 cells (available from Thermo Fisher Scientific) grown as spheroids were grown in McCoy 5a (Fisher Scientific) spiked with 10% fetal bovine serum at 37° C. in 5% $CO_2$ environment for 72 hours.

Example 1: 4-Arm-PEG-($NH_2$)3-FITC, [4-Arm-(PEG-$NH_2$)3-PEG-NH—C(=S)=N-Fluorescein], Mol Wt 5 k, Scheme 1

4-arm PEG $NH_2$ (mol wt 5 k) 0.5 g (0.1 mmol) was dissolved in DMF (dimethyl formamide 10 ml) to which fluorescein isothiocyanate (39 mg, 0.1 mmol) was added under dark. The mixture was stirred at room temperature for 6 hours. The solution was dialyzed in DI water using 1000 mol wt cut off membrane overnight in dark with DI water exchanged 4×1 L. The solution was lyophilized. The bright yellow powder (512 mg) was collected and stored in amber color bottle at −20° C.

Example 2: 4-Arm-PEG-($NH_2$)3-FITC, [4-Arm-(PEG-$NH_2$)3-PEG-NH—C(=S)=NH-Fluorescein], Mol Wt 10 k, Scheme 1

4-arm PEG $NH_2$ (mol wt 10 k) 0.5 g (0.05 mmol) was dissolved in DMF (10 ml) to which fluorescein isothiocyanate (20 mg, 0.05 mmol) was added under dark. The mixture was stirred at room temperature for 6 hours. the solution was dialyzed in DI water using 1000 mol wt cut off membrane overnight in dark with DI water exchanged 4×1 L. The solution was lyophilized. The bright yellow powder (492 mg) was collected and stored in amber color bottle at −20° C.

Example 3: -Arm-PEG-(NHCO-$PEG_4$-DBCO)$_3$—$NH_2$, [4-Arm-Polyethylene Glycol-{NH—CO—($CH_2CH_2$—O)$_3$—$CH_2CH_2$NHCOC$H_2$C$H_2$CO-Dibenzocyclooctyne}3-$NH_2$], Mol Wt 10 k, Scheme 2

4-arm PEG $NH_2$ (mol wt 10 k) 1.0 g (0.1 mmol) was dissolved in methylene chloride (20 ml), to this DBCO-$PEG_4$-NHS ester (195 mg, 0.3 mmol) was added and the mixture was stirred at room temperature for 16 hours. The reaction was monitored by TLC. After the reaction was complete, the solvent was removed under vacuum to 5 ml. The solution was poured drop by drop into cold diethyl ether. The product was precipitated and was collected by filtration. The product was washed thoroughly with ether 4×50 ml and dried under vacuum for 4 hours. The material was obtained as pale yellow powder 1.1 g. It was stored in an amber color bottle at −20° C.

Example 4: 4-Arm-PEG-[NH-$PEG_4$-DBCO)]$_3$-FITC, [4-Arm-Polyethylene Glycol-NH—[CO—($CH_2CH_2$—O)$_3$—$CH_2CH_2$NHCOC$H_2$C$H_2$CO-Dibenzocyclooctyne]-Fluorescein Isthiocyanate], Mol Wt 10 k, Scheme 2

4-arm-PEG-{NHCO-$PEG_4$-DBCO}$_3$—$NH_2$ (mol wt 10 k) 500 mg (0.05 mmol) was dissolved in DMF (5 ml), to which fluorescein isothiocyanate (20 mg, 0.05 mmol) was added under dark. The mixture was stirred at room temperature for 6 hours. The solution was dialyzed in DI water using 1000 mol wt cut off membrane overnight in dark with DI water exchanged 4×1 L. The solution was lyophilized. The bright yellow powder (485 mg) was collected and stored in amber color bottle at −20° C.

Example 5: 4-Arm-PEG-NH-DBCO: 4-Arm-Polyethylene Glycol-{NH—CO—($CH_2$)4-Co-Dibenzocyclooctyne, Mol Wt 10 k, Scheme 3

4-arm PEG $NH_2$ (mol wt 10 k) 1.4 g (0.14 mmol) was dissolved in phosphate buffer, to this DBCO-Sulfo-NHS ester (0.30 g, 0.56 mmol) was added and the mixture was stirred at room temperature for 16 hours. The reaction was monitored by TLC. After the reaction was complete, the reaction mixture was poured drop by drop into cold isopropanol (500 ml) while stirring. The product was precipitated that was collected by filtration. The product was dissolved again in $CH_2Cl_2$ (20 ml) and poured in cold diethyl ether (300 ml). The product was precipitated as powder, which was collected by filtration and washed thoroughly with ether 4×50 ml and dried under vacuum for 4 hours. The material was obtained as pale yellow powder 1.65 g. It was stored in amber color bottle at −20° C.

Example 6: 4-Arm-PEG-NH-$PEG_4$-DBCO: 4-Arm-Polyethylene Glycol-NH—CO—($CH_2CH_2$—O)$_3$—$CH_2CH_2$NCOC$H_2$C$H_2$CO-Dibenzocyclooctyne], Mol Wt 10 k, Scheme 4

4-arm PEG $NH_2$ (mol wt 10 k) 1.4 g (0.14 mmol) was dissolved in methylene chloride (30 ml), to this DBCO-$PEG_4$-NHS ester (0.37 g, 0.56 mmol) was added and the mixture was stirred at room temperature for 16 hours. The reaction was monitored by TLC, after the reaction was complete; the solvent was removed under vacuum to 5 ml. The solution was poured drop by drop into cold diethyl ether. The product was precipitated that was collected by filtration and it was washed thoroughly with ether 4×50 ml and dried under vacuum for 4 hours. The material was obtained as pale yellow powder 1.71 g. It was stored in amber color bottle at −20° C.

Example 7: Synthesis of Click Reactive Co-Polymer of Methacryloyloxyphosphocholine-Allylamine Containing Click Reactive DBCO Groups with PEG Linker (Scheme 5)

A solution of methacryloyloxyphosphocholine-allylamine co-polymer (LIPIDURE®NH-01, 5% polymer solution, 20 ml) was taken into a round bottom flask, to which DBCO-PEG$_4$-NHS ester (400 mg) in DMF (5 ml) was added and the mixture was stirred with a magnetic stir bar at room temperature. Immediately, triethylamine (100 μL) was added to the mixture to maintain the pH around 8.5, the stirring was continued at room temperature for 16 hours. At the end of reaction, the reaction mixture was dialyzed (10K mol wt cut off membrane). The solution was lyophilized. The polymer was obtained as white powder. $^1$H NMR (D$_2$O): 0.96-1.16 (m, CH3); 1.5-2.2 m (backbone CH2); 2.8-3.2 m; 3.8-4.4 m; 4.7 m, 6.8 to 7.3 broad peak (aromatic H).

Example 8: Synthesis of Co-Polymer of Methacryloyloxyphosphocholine-Allylamine Containing Click Reactive Azide Groups (Scheme 6)

A solution of methacryloyloxyphosphocholine-allylamine co-polymer (LIPIDURE®NH-01, 5% polymer solution, 20 ml) was taken into a round bottom flask, to which azido-PEG$_{12}$-NHS ester (400 mg) in DMF (5 ml) was added while the mixture was stirring with a magnetic stir bar at room temperature. Immediately triethylamine (100 microliters) was added to the mixture for maintaining the pH around 8.5, the stirring was continued at room temperature for 16 hours. At the end of reaction, the reaction mixture was dialyzed (10K mol wt cut off membrane). The solution was lyophilized. The polymer was obtained as white powder. $^1$H NMR (D$_2$O): 3.15 (s, quaternary CH3 groups); 3.58 s, 3.9-4.28 (m, —CH2).

Example 9: Synthesis of Click Reactive Co-Polymer of Methacryloyloxyphosphocholine-Allylamine Containing Click Reactive DBCO Groups with Hydrophobic Alkyl Chain Linker (Scheme 7)

A solution of methacryloyloxyphosphocholine-allylamine co-polymer (LIPIDURE®NH-01, 5% polymer solution, 20 ml) was taken into a round bottom flask, to which DBCO-(C6-linker)-sulfoN-hydroxysuccinimide ester (400 mg) powder was added and the mixture was stirred with a magnetic stir bar at room temperature. Immediately, NaHCO$_3$ (100 mg powder) was added to the mixture to maintain the pH around 7.4, the stirring was continued at room temperature for 16 hours. At the end of reaction, the reaction mixture was dialyzed (10K mol wt cut off membrane). The solution was lyophilized. The polymer was obtained as pale yellow cotton like material. $^1$H NMR (D$_2$O): 0.98-1.18 (m, CH3); 1.6-2.2 m; 2.8-3.4 m; 3.9-4.3 m; 4.8 m, 6.9 to 7.3 m (aromatic H).

Example 10: Synthesis of Click Reactive Co-Polymer of Methacryloyloxyphosphocholine-Allylamine Containing Click Reactive DBCO Groups with Fluorescein Tag (Scheme 8)

To a round bottom flask, methacryloyloxyphosphocholine-allylamine containing click reactive DBCO polymer (100 mg) and magnetic stir bar were charged. To the flask, 10 ml of deionized water was added and stirred until the polymer was completely dissolved. The pH of the polymer solution was 7.1, this was adjusted to 8.0 with triethylamine. Fluorescein isothiocyanate 35 mg was weighed in a vial and allowed to dissolve in DMF (5 ml) in dark. The fluorescein isothiocyante solution was added to polymer solution and the mixture was allowed to stir overnight in dark. At the end of reaction, the reaction mixture was dialyzed in dark against deionized water using 10K mol wt cut off membrane. After the completion of dialysis, the contents of the dialysis bag were lyophilized. The product was obtained a bright yellowish sponge like material (120 mg). The product was used directly by mixing with other click reactive polymers for coating the biological surfaces.

Example 11: HCT116 Spheroids: Procedure for HCT116 Cell Spheroids Preparation HCT 116 cell line was seeded into each well at a dose of 500, 1000 and 1500 cells per well which contains 100 microliters of McCoy 5a buffer spiked with 10% fetal bovine serum. The plates were incubated at 37° C. under 5% CO$_2$. After 72 hours, the spheroids were collected and washed with PBS and immediately used for conformal coating.

Example 12: Rat Insulinoma Cell Spheroids: Procedure for Insulinoma Cell Spheroids Preparation Rat insulinoma cells (ins-1 cells) were seeded into each well at a dose of 1000 per well which contains 100 microliters of DMEM medium containing 10% fetal bovine serum. The plates were incubated at 37° C. under 5% CO$_2$. After 72 hours, the spheroids were collected and immediately used for conformal coating.

Example 13: Rat Pancreatic Islets: Procedure for Pancreatic Islets Isolation and Preservation Until Coating Performed Rat islets were isolated from Wistar rats using the collagenase digestion method. Carter et al., *BIOLOGICAL PROCEDURES ONLINE*, vol 11, number 1, 2009. The proximal common bile duct was cannulated with a catheter and slowly injected with 10 ml of cold collagenase solution. Total pancreatectomy was carefully performed to maintain the integrity of the pancreatic capsule. The isolated pancreatic tissue was incubated in additional 5 ml of collagenase solution for 20 minutes at 37° C., and then the tissue was disintegrated under vigorous shaking. After washed twice with 30 ml of cold HBSS buffer containing 0.02% DNase I and 1% bovine serum albumin, it was passed through a wire mesh screen followed by centrifugation at 1300 rpm for 3 minutes at 4° C. Then the mass was suspended in 10 ml of histopaque-1077 solution. The tissue suspension was overlayered with a 10 ml of HBSS buffer containing 0.02% DNase I and 1% bovine serum albumin followed by gradient centrifugation at 1800 rpm for 3 minutes at 4° C. Purified islets were collected from the interface between the top and the second layer with pipette, and then washed with RPMI-1640 medium repeatedly. The washed islets were preserved under storage in ice, and immediately used for conformal coating.

Example 14: Conformal Coating Methods: Conformal Coating of Polystyrene (PS) Particles with Activated Ester Approach in Sucrose as Suspending Medium Followed by Vacuum Dried Prior to Coating Polystyrene (PS) particles (106 to 125 micron size) 50 mg, 4-arm PEG-NH$_2$ (5 k) 50 mg and 4-arm PEG(NH$_2$)3-FITC (5 k) 200 microliters 1% solution was mixed with 400 microliters of water. The paste was vacuum dried at 30° C. on vacuum centrifuge for 6 hours. The pellet was suspended in 250 microliters of sucrose solution (60%). Freshly prepared solution of activated 4-arm PEG-NHS ester (5 k), (20 mg was dissolved in 80 microliters water) was added to the PS particles in sucrose solution while vortexed at 2000 rpm for 3 minutes. The mixture was centrifuged at 4° C. at 3000 rpm for 5 minutes and the supernatant was removed. The pellet was suspended in PBS (2 ml) and vortexed to disperse the coated particles uniformly in solution and centrifuged again at 4° C., 3000 rpm for 5 minutes. The washing procedure was repeated for 5 times to remove the excess un-reacted polymers and sucrose. The coated particles were transferred into wells for microscopic evaluation. The confocal microscopic images revealed that the particles were uniformly coated as visualized under fluorescence filed, FIG. 1.

Example 15: Conformal Coating of Polystyrene Particles with 4-Arm PEG-NHS Activated Ester (10 k) in PEO (8 Million Mol. Wt.) 1% Solution as Suspending Medium of Top Layer To a 2 ml centrifuge tube, 100 microliters of 15% sucrose solution was loaded (layer 3). On top of this 200 microliters of 2.5% sucrose solution containing 4-arm PEG-NHS, 10 k, 20 mg was layered (2nd layer). On top of it a mixture of solution containing polystyrene particles 1 mg, 4-arm PEG-$NH_2$ (10 k, 5 mg), 4-arm PEG-$(NH_2)$3-FITC 10 k (5 microliters, 1% solution in DI water) and PEO (8 million mol wt) 50 microliters of 1% solution was layered (layer 1). The tube was closed tightly and centrifuged at 1000 rpm for 60 minutes at 4° C.

The coated PS particles were settled at the bottom, the supernatant liquid was removed carefully and replaced with fresh DI water (2 ml) and vortexed to disperse the bed in liquid uniformly and centrifuged it again at 1000 rpm for 3 minutes. The supernatant was removed and replaced with fresh water and vortexed to disperse the bed. The washing procedure was repeated 4 times. Finally, the coated particles were placed in wells for confocal microscopic study. The confocal microscopic images under fluorescence field revealed that the polystyrene particles were uniformly coated, FIG. 2.

Example 16: Conformal Coating of Polystyrene Particles with 4-Arm PEG-NHS Ester (10 k) in PEO (4 Million Mol Wt) 1% Solution as Suspending Medium of Top Layer To a 2 ml centrifuge tube, 100 microliters of 15% sucrose solution was loaded (layer 3). On top of this 200 microliters of 2.5% sucrose solution containing 4-arm PEG-NHS, (10 k, and 20 mg) was layered (2nd layer). On the top of it a mixture of solution containing polystyrene particles 1 mg, 4-arm PEG-$NH_2$ (5 mg, 10 k), 4-arm PEG-$(NH_2)$3-FITC (10 k, 5 microliters, 1% solution in DI water) and PEO (4 million mol wt) 50 microliters of 1% solution was layered (layer 1). The tube was closed tightly and centrifuged at 1000 rpm for 60 minutes at 4° C.

The coated polystyrene particles were settled at the bottom; supernatant liquid was removed carefully and replaced with fresh DI water (2 ml). It was vortexed to disperse the bed in liquid and centrifuged again at 1000 rpm for 3 minutes. The supernatant was removed and replaced with fresh water and vortexed to disperse the bed. The washing procedure was repeated 4 times. At the end, the coated particles were placed in wells for confocal microscopic study. The confocal microscopic images under fluorescence field revealed that the particles were uniformly coated, FIG. 3.

Example 17: Conformal Coating of Polystyrene Particles with 4-Arm PEG-NHS Activated Ester (10 k) in PEO (1 Million Mol Wt) 1% Solution as Suspending Medium of Top Layer To a 2 ml centrifuge tube, 100 microliters of 15% sucrose solution was loaded (layer 3). On top of it, 200 microliters of 2.5% sucrose solution containing 4-arm PEG-NHS, (10 k) 20 mg was layered (2nd layer). On top of it a mixture of solution containing polystyrene particles 1 mg, 4-arm PEG-$NH_2$ (10 k, 5 mg), 4-arm PEG-$(NH_2)$3-FITC, (10 k, 5 microliters, 1% solution in DI water) and PEO (1 million mol wt) 50 microliters of 1% solution was layered (layer 1). The tube was closed tightly and centrifuged at 1000 rpm for 60 minutes at 4° C.

The coated polystyrene particles were settled at the bottom; the supernatant liquid was removed carefully and replaced with fresh DI water (2 ml). It was vortexed to disperse the bed in liquid and centrifuged again at 1000 rpm for 3 minutes. The supernatant was removed and replaced with fresh water and vortexed to disperse the bed. The washing procedure was repeated 4 times. Finally, the coated particles were placed in wells for confocal microscopic study. The confocal microscopic images under fluorescence field revealed that the polystyrene particles were less uniformly coated in PEO 1 million mol wt suspending agent compared to PEO 8 million or 4 million suspending agents, FIGS. 4, 3 and 2.

Example 18: Conformal Coating of Polystyrene Particles with Click Reactive Polymers in PEO (1 Million Mol Wt) 1% Solution as Suspending Medium of Top Layer To a 2 ml centrifuge tube, 100 microliters of 10% sucrose solution was loaded (layer 3). On top of it, 200 microliters of 5% sucrose solution containing 4-arm PEG-azide (10 k mol wt) 10 mg was layered (2nd layer). Again on the top of the $2^{nd}$ layer, a mixture of solution containing PS particles 1 mg, 4-arm PEG-NH-DBCO, (10 k, 1.25 mg), 4-arm-PEG-[NH-$(PEG)_4$-dbco)]$_3$-FITC (10 k, 1.25 microliters, 1% solution in DI water) and PEO (1 million mol wt) 50 microliters of 1% solution was layered (layer 1). The tube was closed tightly and centrifuged at 1000 rpm for 10 minutes at 4° C.

The coated particles were settled at the bottom. The supernatant liquid was removed carefully and replaced with fresh DI water (2 ml). It was vortexed to disperse the bed in the liquid and centrifuged again at 1000 rpm for 3 minutes. The supernatant was removed and replaced with fresh water and vortexed to disperse the bed. The washing procedure was repeated 4 times. Finally, the washed coated particles were placed in wells for confocal microscopic study. The confocal microscopic images under fluorescence field revealed that the beads were uniformly coated. See FIG. 5.

Example 19: Conformal Coating of Polystyrene Particles with Click Reactive Polymers in PEO (8 Million Mol Wt) 1% Solution as Suspending Medium of Top Layer To a 2 ml centrifuge tube, 100 microliters of 10% sucrose solution was loaded (layer 3). On to this 200 microliters of 5% sucrose solution containing 4-arm peg-azide (10 k mol wt) 10 mg was layered (2nd layer). On the top of the second layer, a mixture of solution containing PS particles 1 mg, 4-arm PEG-NH-DBCO (10 k, 1.25 mg), 4-arm-PEG-[NH-(PEG)$_4$-DBCO]$_3$-FITC (10 k, 1.25 microliters, 1% solution in DI water) and PEO (8 million mol wt) 50 microliters of 1% solution was layered (layer 1). The tube was closed tightly and centrifuged at 1000 rpm for 10 minutes at 4° C.

The coated beads were settled at the bottom. The supernatant liquid was removed carefully and replaced with fresh DI water (2 mL) and vortexed to disperse the bed in the liquid and centrifuged again at 1000 rpm for 3 minutes. The supernatant was removed and replaced with fresh water and vortexed to disperse the bed. The washing procedure was repeated 4 times. Finally, the washed coated particles were placed in wells for confocal microscopic study. The confocal microscopic images under fluorescence field revealed that the PS particles in PEO 8 million mol wt suspending medium were less uniformly coated compared to PEO 1 million mol wt suspending medium. See FIGS. 5 and 6.

Example 20: Conformal Coating Method of HCT116 Cell Spheroids (500 Cells Initial Dose Per Spheroid) with Click Reactive Polymers in PEO in 1 Million Mol Wt 1% Solution as Suspending Medium of Top Layer To a 2 ml centrifuge tube, 200 microliters of 10% sucrose solution containing 4-arm peg-azide (10 k mol wt) 10 mg was loaded (2nd layer). On the top of it, a mixture of solution containing HCT-116 cell spheroids (30 spheroids), 4-arm PEG-NH-DBCO (10 k, 1.25 mg), 4-arm-PEG-[NH-(PEG)$_4$-DBCO]$_3$-FITC (10 k, 1.25 microliters, 1% solution in DI water) and PEO (1 million mol wt, 50 microliters, 1% solution in saline) was layered as 1$^{st}$ layer. The tube was closed tightly and centrifuged at 1000 rpm for 3 minutes at 4° C.

The coated cell spheroids were settled at the bottom. The supernatant liquid was removed carefully and replaced with fresh McCoy 5a buffer (spiked with 10% fetal bovine serum, 2 ml) and vortexed to disperse the bed in the liquid and centrifuge again at 1000 rpm for 3 minutes. The supernatant was removed and replaced with 3 ml of fresh buffer and vortexed to disperse the bed. The washing procedure was repeated 4 times. Finally, the coated cell spheroids with buffer were placed in wells for confocal microscopic study. The confocal microscopic images under fluorescence field revealed that the HCT116 cell spheroids were less uniformly coated compared to PEO 4 and 8 million mol wt suspending medium, FIG. 7.

Example 21: Conformal Coating of HCTcell 116 Spheroids (500 Cells Initial Dose Per Spheroid) with Click Reactive Polymers in PEO (4 Million Mol Wt) 1% Solution as Suspending Medium of Top Layer To a 2 ml centrifuge tube, 200 microliters of 10% sucrose solution containing 4-arm PEG-azide (10 k mol wt, 10 mg) was loaded (2nd layer, bottom layer). On the top of it, a mixture of solution containing HCT-116 spheroids (30 spheroids), 4-arm PEG-NH-DBCO (1.25 mg), 4-arm-PEG-[NH-PEG$_4$-DBCO]$_3$-FITC (10 k, 1.25 microliters of 1% solution in DI water) and PEO (4 million mol wt, 50 microliters of 1% solution in saline) was layered (1st layer, top layer). The tube was closed tightly and centrifuged at 1000 rpm for 3 minutes at 4° C.

The coated spheroids were settled at the bottom. The supernatant liquid was removed carefully and replaced with fresh McCoy 5a buffer (spiked with 10% fetal bovine serum, 2 ml). It was vortexed to disperse the bed in the liquid and centrifuged again at 1000 rpm for 3 minutes. The supernatant was removed and replaced with 3 ml of fresh buffer and vortexed to disperse the bed. The washing procedure was repeated 4 times. Finally, the coated cell spheroids with buffer were placed in wells for confocal microscopic study. The confocal microscopic images under fluorescence field revealed that the HCT116 cell spheroids were uniformly coated and found better compared to PEO 1 million mol wt suspending medium, FIG. 8.

Example 22: Conformal Coating of HCT116 Cell Spheroids (500 Cells Initial Dose Per Spheroid) with Click Reactive Polymers in PEO (8 Million Mol Wt) 1% Solution as Suspending Medium of Top Layer To a 2 ml centrifuge tube, 200 microliters of 10% sucrose solution containing 4-arm PEG-azide (10 k mol wt, 10 mg) was loaded (2nd layer, bottom layer). On the top of it, a mixture of solution containing HCT-116 cell spheroids (30 spheroids), 4-arm PEG-NH-DBCO (1.25 mg), 4-arm-PEG-[NH-(PEG)$_4$-DBCO]$_3$-FITC (10 k, 1.25 microliters, 1% solution in DI water) and PEO (8 million mol wt, 50 microliters, 1% solution in saline) was layered (1st layer, top layer). The tube was closed tightly and centrifuged at 1000 rpm for 3 minutes at 4° C.

The coated spheroids were settled at the bottom. The supernatant liquid was removed carefully and replaced with fresh McCoy 5a buffer (spiked with 10% fetal bovine serum, 2 ml). It was vortexed to disperse the bed in the liquid and centrifuge again at 1000 rpm for 3 minutes. The supernatant was removed and replaced with 3 ml of buffer and vortexed to disperse the bed. The washing procedure was repeated 4 times. Finally, the coated cell spheroids with buffer were placed in wells for confocal microscopic study. The confocal microscopic images under fluorescence field revealed that the HCT116 cell spheroids were uniformly coated and found to be better compared to PEO 1 million suspending medium, FIG. 9.

Example 23: Conformal Coating of HCT116 Cell Spheroids (1000 Cells Initial Dose Per Spheroid) with Click Reactive Polymers in PEO (8 Million Mol Wt) 1% Solution as Suspending Medium in Top Layer To a 2 ml centrifuge tube, 200 microliters of 10% sucrose solution containing 4-arm PEG-azide (10 k mol wt, 20 mg was loaded (2nd layer, bottom layer). On the top of it, a mixture of solution containing HCT-116 cell spheroids (30 spheroids), 4-arm PEG-NH-DBCO (2.5 mg), 4-arm-PEG-[NH-(PEG)$_4$-DBCO]$_3$-FITC (10 k, 2.5 microliters, 1% solution in DI water) and PEO (8 million mol wt, 50 microliters, 1% solution in saline) was layered (1st layer, top layer). The tube was closed tightly and centrifuged at 1000 rpm for 3 minutes at 4° C.

Figure 10:
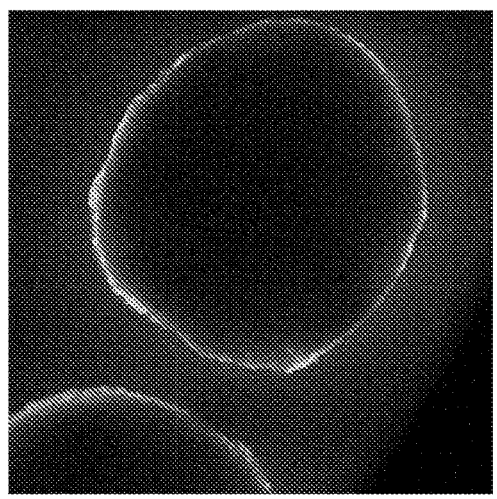
FIG. 10 is a confocal micrograph of coated HCT116 1000 cells/spheroid; PEO (8 million mol wt) 4-arm PEG-DBCO: 4-arm PEGazide.

The coated spheroids were settled at the bottom and the supernatant liquid was removed carefully followed by the addition of fresh McCoy 5a buffer 2 ml (spiked with 10% fetal bovine serum). The tube was vertex to disperse the bed uniformly in liquid and centrifuged again at 1000 rpm for 3 minutes. The supernatant was removed and replaced with 3 ml of fresh McCoy 5a buffer and vortexed again to disperse the bed. The washing procedure was repeated 4 times. Finally, the coated spheroids were placed in wells for confocal microscopic study. The confocal microscopic images under fluorescence revealed uniformly coated as shown, FIG. 10.

Example 24: Live/Dead Cell Assay

Live cells are distinguished by intracellular esterase activity, which is determined by the enzymatic conversion of the virtually non-fluorescent Calcein AM into fluorescent Calcein moiety. Calcein AM dye is a poly anionic dye that is retained within live cells and react with intracellular esterase to produce an intense green fluorescence at ex/em 495 nm/515 nm. In contrast, ethidium homodimer-1 (EthD-1) enters the cells with damaged membranes of dead cells and undergoes 40-fold enhancement of fluorescence upon binding with nucleic acids to give bright red fluorescence at ex/em 495/635 nm. Ethd-1 is excluded by the intact plasma membrane of live cells. The combined of these two dyes would give the picture of live/dead cells of a given sample.

Example 25: Live/Dead Cell Assay Procedure

Twenty microliters of 2 mM Ethd-1 stock solution was taken into a 10 ml sterile tissue culture grade Dulbecco PBS. Five micro-liters of 4 mM Calcein AM solution in DMSO was added to the Ethd-1 solution and the mixture was vortex. The resulting live/dead test reagent has 2 micromole Calcien per 4 micro mole EthD-1 in the solution. Each well of multi-well plate was loaded with 100 microliters of cell-containing test solution, to which 100 microliters of live/dead test reagent was added and incubated at 37° C. for 30 minutes. The cells were evaluated on confocal microscope at two different wavelengths ex/em~495 nm/~515 nm and 495/635 nm.

Example 26: Microscopic Examination and Live/Dead Viability Assay of Coated and Naked HCT116 Cell Spheroids The coated HCT cell 116 spheroids (1000 cells initial dose/spheroid) were freshly prepared and divided into two portions. Conformal coating was applied to one portion with 4-arm PEG-DBCO and 4-armPEG azide as described in Example 19. Both coated and naked cell spheroids were evaluated immediately for cell viability using the Calcein AM/EthD-1 assay. The coated spheroids as well as naked spheroids have viable cells initially and there were no dead cells. On aging at 37° C., in McCoy 5a buffer under 5% $CO_2$, the cell death was significantly high in naked spheroid (FIG. 11) compared to the coated cell spheroids at day 3, FIG. 12.

Example 27: Conformal Coating of Insulinoma Cell Spheroids with Click Reactive Polymers in PEO (1 Million Mol Wt) 1% Solution as Suspending Medium of Top Layer To a 2 ml centrifuge tube, 200 microliters of 10% sucrose solution containing 4-arm PEG-azide (10 k mol wt, 10 mg) was loaded as 2nd layer (bottom layer). On the top of it, a mixture of solution containing insulinoma spheroids (1000 spheroids), 4-arm PEG-NG-DBCO (2.5 mg), 4-arm-PEG-[NH-$(PEG)_4$-DBCO]$_3$-FITC (10 k, 2.5 microliters, 1% solution in DI water) and PEO (1 million mol wt, 50 microliters, 1% solution in saline) was layered (1st layer). The tube was closed tightly and centrifuged at 1000 rpm for 3 minutes at 4° C.

The coated spheroids were settled at the bottom and the supernatant liquid was removed carefully followed by the addition of saline 2 ml. The tube was vortexed to disperse the bed in the liquid and centrifuged again at 1000 rpm for 3 minutes. The supernatant was removed and replaced with fresh saline 2 ml, and it was vortexed to disperse the bed. The washing procedure was repeated 4 times. Finally, the washed coated spheroids were placed in wells for fluorescence microscopic study. The fluorescence microscopic images revealed that the insulinoma cell spheroids were uniformly coated, FIG. 13.

Example 28: Conformal Coating of Rat Pancreatic Islets with Click Reactive Polymers in PEO (1 Million Mol Wt) 1% Solution as Suspending Medium in Top Layer To a 2 ml centrifuge tube, 200 microliters of 10% sucrose solution containing 4-arm PEG-azide (10 k mol wt, 10 mg) was loaded (2nd layer, bottom layer). On the top of it, a mixture of solution containing pancreatic islets (100 islets), 4-arm PEG-NH-DBCO (2.5 mg), 4-arm-PEG-[NH-$(PEG)_4$-DBCO]$_3$-FITC (10 k, 2.5 microliters, 1% solution in DI water) and PEO (1 million mol wt, 50 microliters, 1% solution in saline) was layered (1st layer, top layer). The tube was closed tightly and centrifuged at 1000 rpm for 3 minutes at 4° C.

The coated islets were settled at the bottom and the supernatant liquid was removed carefully followed by the addition of fresh saline 2 ml. The tube was vortexed to disperse the bed in the liquid and centrifuged again at 1000 rpm for 3 minutes. The supernatant was removed and replaced with fresh saline 2 ml and it was vortexed to disperse the bed. The washing procedure was repeated 4 times. Finally, the washed coated islets were placed in wells for fluorescence microscopic study. The fluorescence microscopic images revealed that the pancreatic islets were coated as shown, FIG. 14.

Figure 19:
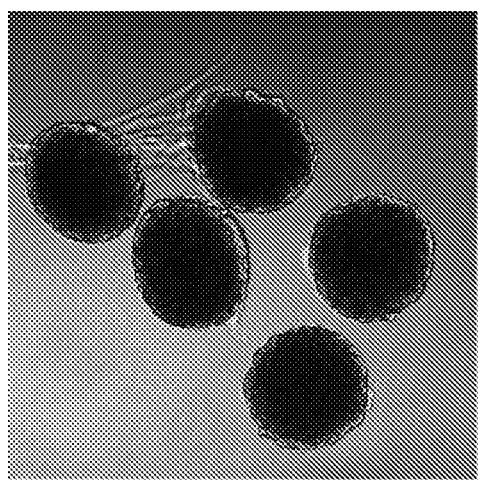
FIG. 19-21 are confocal microscopic images of the stability of coated ARPE-19 spheroids, which were coated with click reactive MPC polymers using suspending agent in 1st layer (Top layer).
Figure 20:
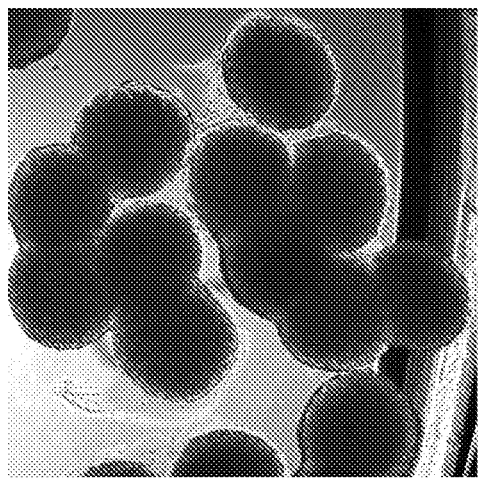
Figure 21:
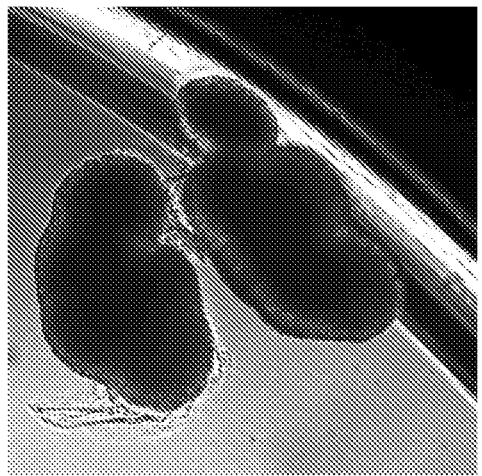
Figure 22:
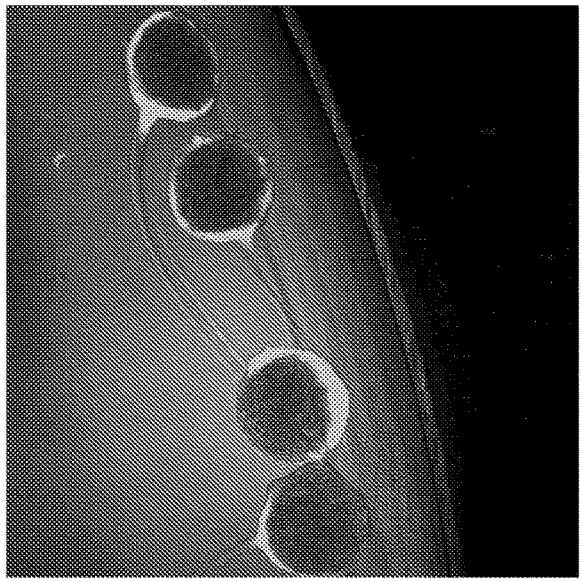
FIG. 22-28 are confocal microscopic images of the stability of ARPE-19 spheroids which, were coated with click reactive MPC polymers using suspending agent in both layers.

Example 29: Conformal Coating of ARPE-19 Cell Spheroids with Click Reactive MPC Polymers with PEO Solution as Suspending Medium in Top Layer To a 2 ml centrifuge tube, 200 microliters of 10% sucrose solution containing azide-modified MPC polymer (10 mg) was loaded as 2nd layer (bottom layer). On the top of it, a mixture of solution containing ARPE-19 spheroids (50 spheroids), DBCO-modified MPC polymer (2.5 mg), FITC-labeled DBCO-modified MPC polymer (0.025 mg) and PEO (1 million mol wt, 50 microliters, 1% solution in saline) was layered (1st layer). The tube was closed tightly and centrifuged at 1000 rpm for 3 minutes. The coated spheroids were settled at the bottom and the supernatant liquid was removed carefully followed by the addition of saline 2 ml. The tube was vortexed to disperse the bed in the liquid and centrifuged again at 1000 rpm for 3 minutes. The supernatant was removed and replaced with fresh PBS 2 ml, and it was vortexed to disperse the bed. The washing procedure was repeated 3 times. Finally, the washed coated spheroids were placed in wells and cultured in DMEM medium at 37° C. for confocal microscopic study. The confocal microscopic images revealed that the ARPE-19 cell spheroids were uniformly coated, and gradually fused with the coated polymer removal over time, FIG. 19-21.

Example 30: Conformal Coating of ARPE-19 Cell Spheroids with Click Reactive MPC Polymers in PEO Solution as Suspending Medium in Both Layers To a 2 ml centrifuge tube, 200 microliters of 10% sucrose solution containing azide-modified MPC polymer (10 mg) and PEO (1 million mol wt, 2 mg) was loaded as 2nd layer (bottom layer). On the top of it, a mixture of solution containing ARPE-19 spheroids (50 spheroids), DBCO-modified MPC polymer (2.5 mg), FITC-labeled DBCO-modified MPC polymer (0.025 mg) and PEO (1 million mol wt, 50 microliters, 1% solution in saline) was layered (1st layer). The tube was closed tightly and centrifuged at 1000 rpm for 3 minutes. The coated spheroids were settled at the bottom and the supernatant liquid was removed carefully followed by the addition of saline 2 ml. The tube was vortexed to disperse the bed in the liquid and centrifuged again at 1000 rpm for 3 minutes. The supernatant was removed and replaced with fresh PBS 2 ml, and it was vortexed to disperse the bed. The washing procedure was repeated 3 times. Finally, the washed coated spheroids were placed in wells and cultured in DMEM medium at 37° C. for confocal microscopic study. The confocal microscopic images revealed that the ARPE-19 cell spheroids were uniformly coated, stable and not fused beyond 2 months FIG. 22-28.

Figure 29:
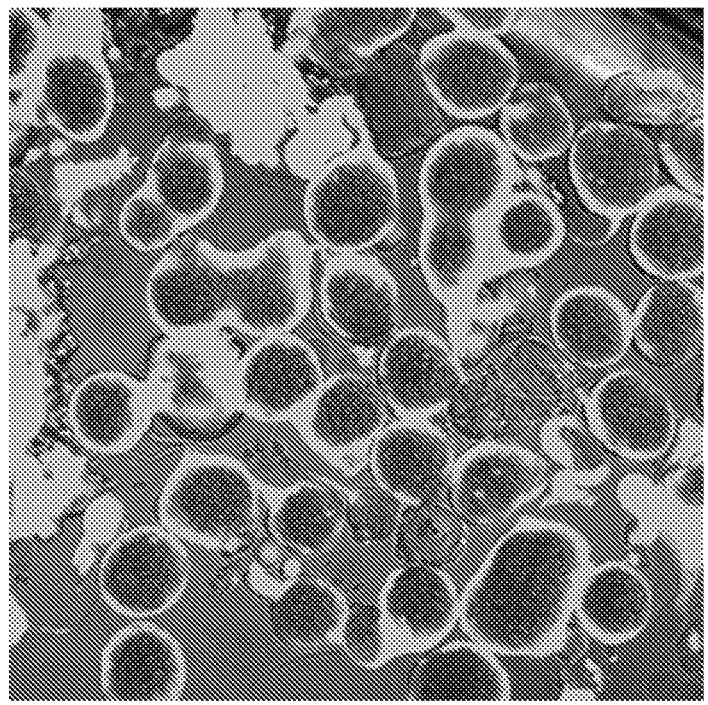
FIG. 29 is a confocal microscopic image ARPE-19 spheroids coated by continuous addition method.
Figure 30:
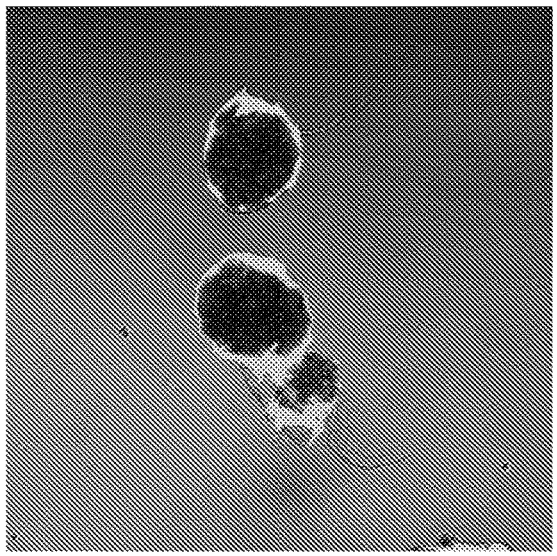
FIGS. 30-33 are confocal microscopic images of the stability of coated rat pancreatic Islets by continuous addition method using MPC click reactive polymers.
Figure 31:
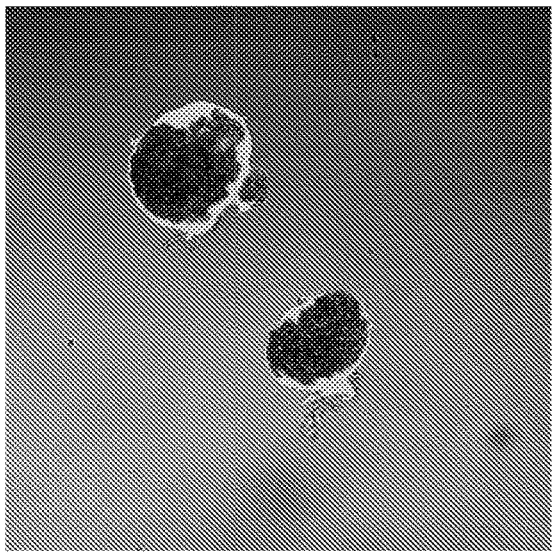
Figure 32:
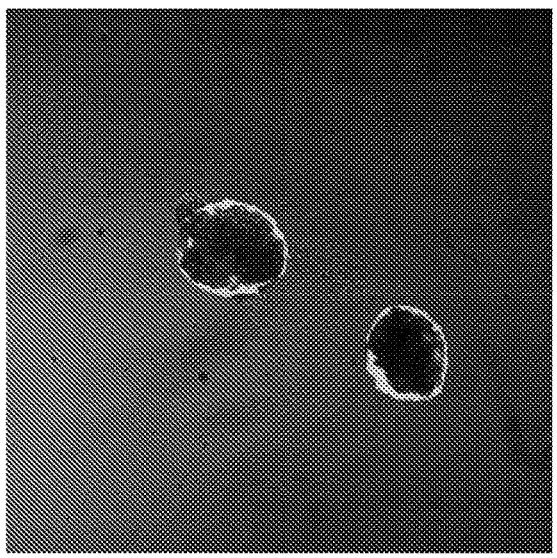
Figure 33:
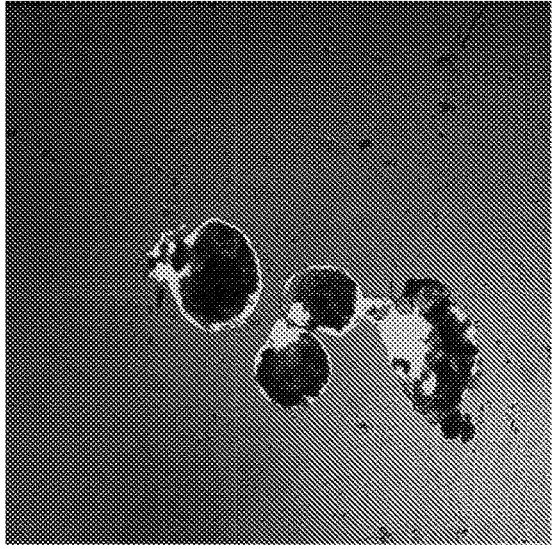
Figure 34:
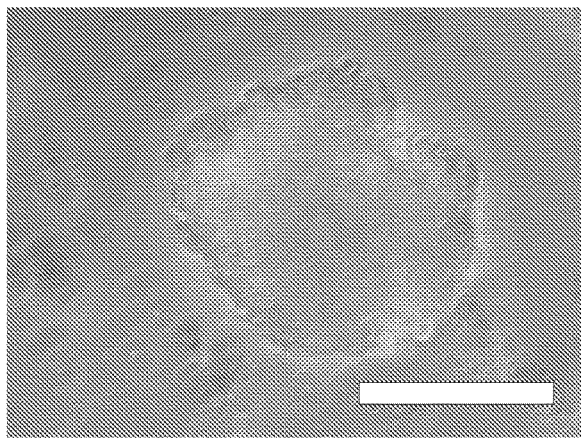
FIGS. 34-37 are confocal microscopic images of the live/dead viability of naked and coated rat pancreatic islets; islets coated by continuous addition method using click reactive MPC polymers.
Figure 35:
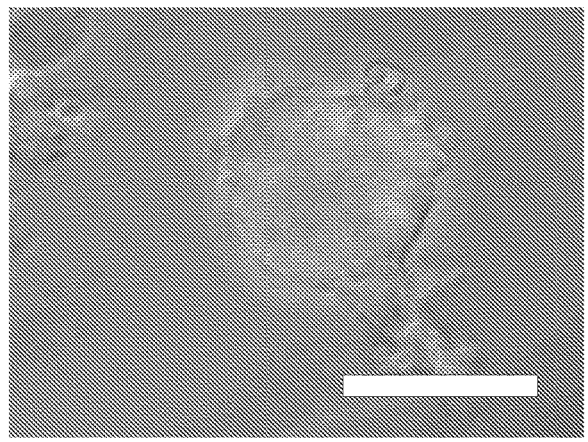
Figure 36:
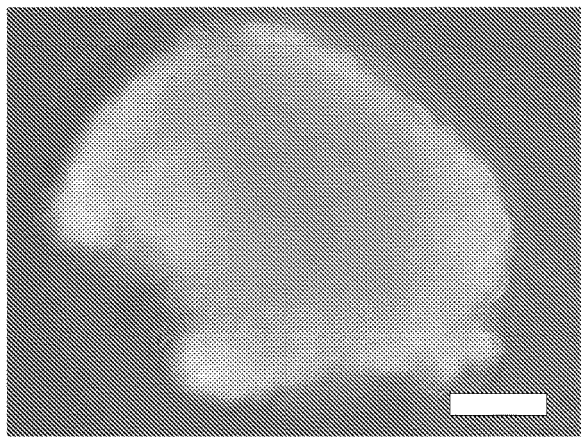
Figure 37:
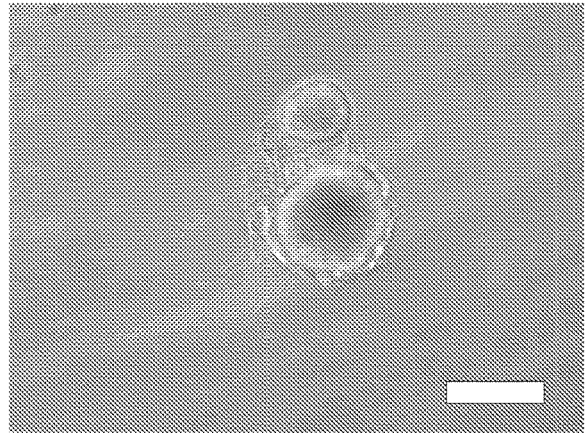

Example 31: Conformal Coating of ARPE-19 Cell Spheroids with Click Reactive Polymers Using Suspending Medium in Both Layers and by Continuous Addition Method of Top Layer 10 microliters of the 200 ARPE-19 spheroids-suspended saline solution containing DBCO-modified MPC polymer (0.5 mg), FITC-labeled DBCO-modified MPC polymer (0.05 mg) and PEO (1 million mol wt, 0.1 mg) was introduced into the pipette tip, and assembled in the microtube which was filled with 200 microliters of 10% sucrose solution containing azide-modified MPC polymer (10 mg) and PEO (1 million mol wt, 2 mg) at the bottom. The microtube was centrifuged using a table-top centrifuge at 1000 rpm for 3 min. The coated spheroids were settled at the bottom and the supernatant liquid was removed carefully followed by the addition of saline 2 ml. The tube was vortexed to disperse the bed in the liquid and centrifuged again at 1000 rpm for 3 minutes. The supernatant was removed and replaced with fresh PBS 2 ml, and it was vortexed to disperse the bed. The washing procedure was repeated 3 times. Finally, the washed coated spheroids were placed in wells and cultured in DMEM medium at 37° C. for confocal microscopic study. The confocal microscopic images revealed that the ARPE-19 cell spheroids were uniformly coated and obtained with high yield ratio, FIG. 29.

Example 32: Conformal Coating of Rat Pancreatic Islets with Click Reactive MPC Polymers Using Suspending Medium in Both Layers and by Continuous Addition Method of Top Layer Fifty islets (5 microliter volume) were suspended saline solution containing DBCO-modified MPC polymer (0.25 mg), FITC-labeled DBCO-modified MPC polymer (0.025 mg) and PEO (1 million mol wt, 0.05 mg) was introduced into the pipette tip, and assembled in the microtube which was filled with 100 microliters of 10% sucrose solution containing azide-modified MPC polymer (5 mg) and PEO (1 million mol wt, 1 mg) at the bottom. The microtube was centrifuged using a table-top centrifuge at 1000 rpm for 3 min. The coated islets were settled at the bottom and the supernatant liquid was removed carefully followed by the addition of saline 2 mL. The tube was vortexed to disperse the bed in the liquid and centrifuged again at 1000 rpm for 3 minutes. The supernatant was removed and replaced with fresh PBS 2 mL, and it was vortexed to disperse the bed. The washing procedure was repeated 3 times. Finally, the washed coated islets were placed in wells and cultured in RPMI medium at 37° C. for confocal microscopic study. The confocal microscopic images revealed that the islets were uniformly coated, and the coated polymer stably existed up to 26 days, FIG. 30-33.

Example 33: Insulin Secretion Study of Coated Insulinoma Cell Spheroids of Example 27 in Comparison with Naked Insulinoma Cell Spheroids The coated insulinoma spheroids and naked insulinoma spheroids (100 spheroids each) were placed in wells containing 1 mL of 1 millimolar glucose Krebs buffer (Sigma) for 1 hour at 37° C. for equilibration and for pre-incubation. This was followed by sequential incubation for 2 hour in low glucose (3 millimolar, 1 mL), high glucose (10 millimolar, 1 mL) and low glucose (3 millimolar, 1 mL) Krebs buffer at 37° C. At the end of incubation in low glucose buffer, 100 microliters of the supernatant were collected for assay. For high glucose buffer, at each time point (10, 30, 60, 90, 120 minutes) 30 microliters of the supernatant were collected for assay and again for low glucose buffer 100 microliters of supernatant was collected for assay. The collected samples were assayed by ELISA. Insulin secretion responsiveness to glucose was confirmed for both coated and naked spheroids, and insulin secretion of coated spheroids was comparable to naked spheroids in high glucose buffer. See FIG. 15. There was no delay of insulin secretion for coated spheroids in high glucose buffer was observed and it is relative to naked spheroids, but found superior to microencapsulated (barium/alginate) formulations. The data was plotted in FIG. 16.

Example 34: Insulin Secretion Study Using Coated Rat Pancreatic Islets of Example 28 in Comparison with Naked Islets The coated rat islets and naked islets (20 islets each) were placed in wells containing 1 ml of 1 millimolar glucose Krebs buffer for 1 hour at 37° C. for equilibration and for pre-incubation. This was followed by sequential incubation for 2 hour in low glucose (2 mM, 1 mL), high glucose (20 mM, 1 mL) and low glucose (2 mM, 1 mL) Krebs buffer at 37° C. At the end of incubation in low glucose buffer, 100 microliters of the supernatant were collected for assay. For high glucose buffer, at each time point (10, 30, 60, 90, 120 minutes) 30 microliters of the supernatant were collected for assay and again for low glucose buffer 100 microliters of supernatant was collected for assay. The collected samples were assayed by ELISA. Insulin secretion responsiveness to glucose was confirmed for both coated and naked spheroids, and insulin secretion of coated islets was comparable to naked islets in high glucose buffer FIG. 17. There was no delay of insulin secretion for coated spheroids in high glucose buffer was observed and it is relative to naked spheroids, but found superior to microencapsulated (barium/alginate) formulations. The data was plotted in FIG. 18.

Example 35: Microscopic Examination and Live/Dead Viability Assay of Coated Islets by Continuous Addition Method of Example 32 and Naked Rat Islets Islets were briefly rinsed with Dulbecco's Phosphate Buffer Saline (DPBS) and incubated for 30 min in a DPBS composed of 4 µM calcein AM and 8 µM ethidium homodimer-1 (EthD-1). The viability of islets was evaluated on a confocal microscope. The coated spheroids as well as naked spheroids have almost all viable cells initially. On aging in culture medium, naked islets caused central cell necrosis due to aggregation of each other at Day 29, while coated islets were still alive to avoid an aggregation by the effect of coated polymer FIG. 34-37

Figure 38:
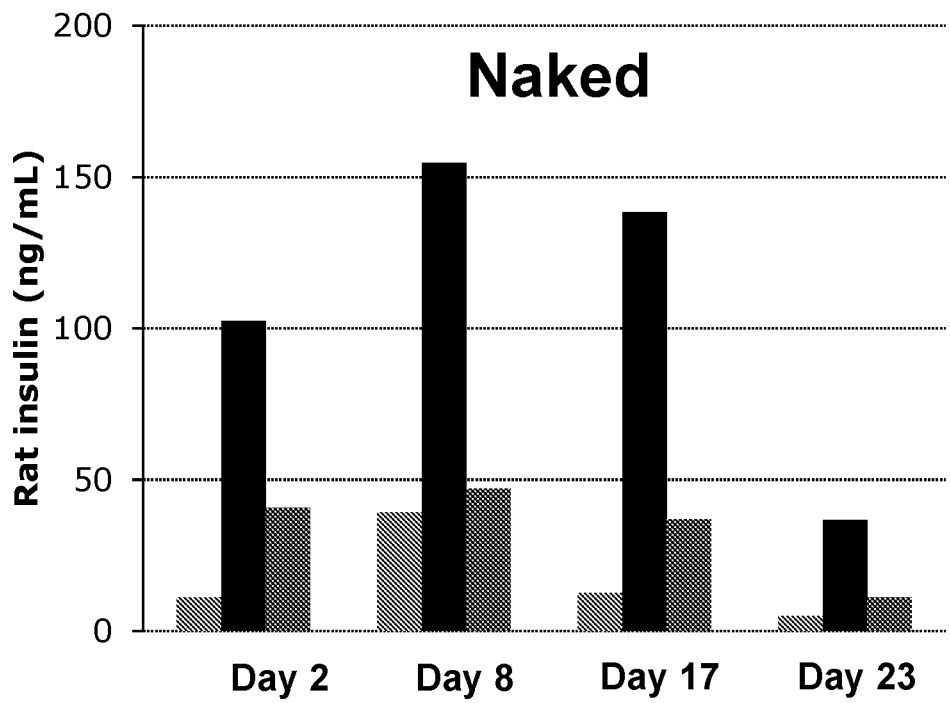
FIGS. 38-39 are a bar graphs summarizing rat pancreatic islets insulin secretion of naked islets and the Islets coated by continuous addition method using click reactive MPC polymers.
Figure 39:
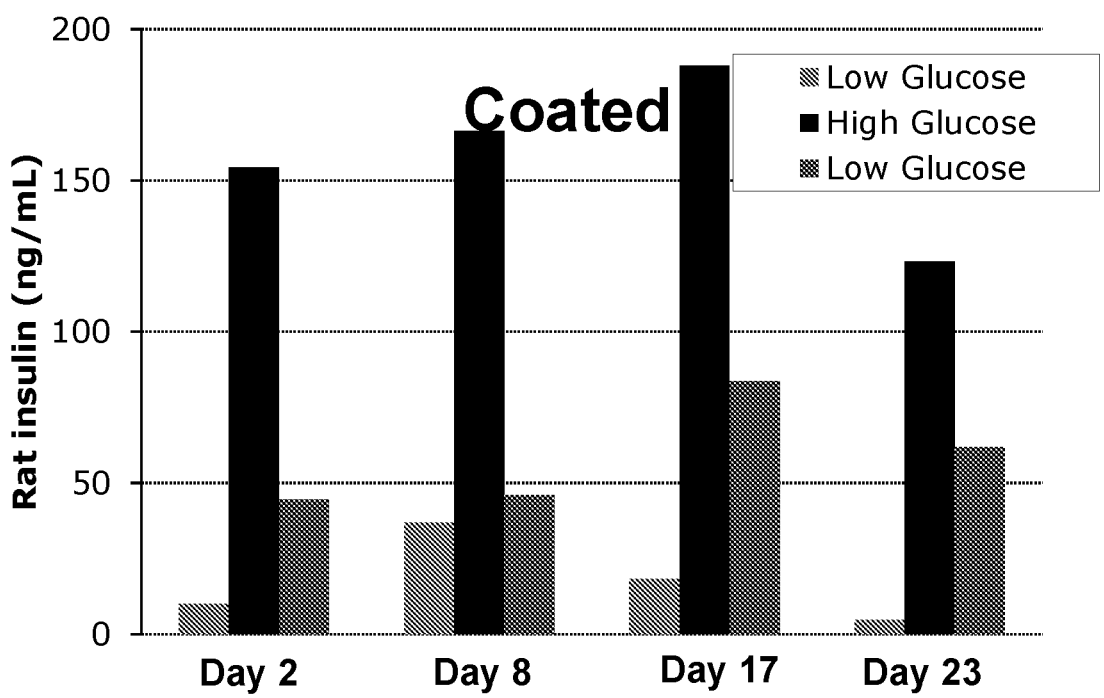

Example 36: Insulin Secretion Study of Rat Pancreatic Islets Coated by Continuous Addition Method of Example 32 in Comparison with Naked Islets The coated rat islets and naked islets (20 islets each) were placed in wells containing 1 mL of 1 mM glucose Krebs buffer for 1 hour at 37° C. for equilibration and for pre-incubation. This was followed by sequential incubation for 2 hour in low glucose (2 mM, 1 mL), high glucose (20 mM, 1 mL) and low glucose (2 mM, 1 mL) Krebs buffer at 37° C. At the end of incubation in each glucose buffer, 100 µl of the supernatant were collected for assay. The collected samples were assayed by ELISA, insulin secretion function of both naked and coated islets was found to be consistent under in vitro culture until day 17, however, naked islets significantly decreased their function at day 23, while coated islets still maintained their function, FIG. 38,39.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The foregoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

The invention claimed is:

1. A composition comprising a living cell having a hydrogel conformal coating on the cell's surface, wherein the conformal coating is uniform over the entirety of the surface of the cell, wherein the thickness of the conformal coating is less than about 20 µm, wherein the hydrogel conformal coating comprises a covalently cross-linked network of multi arm polymers that cross-link through a triazole linkage; wherein the network of multi arm polymers comprises polyethylene glycol (PEG), a methacryloyloxyethyl phosphocholine co-polymer, or a combination thereof.

2. The composition of claim 1, wherein the network of multi arm polymers comprises a 4-arm 5-10 kDa polyethylene glycol (PEG); or a methacryloyloxyethyl phosphocholine co-polymer that is 100-200 kDa and 60-90% phosphocholine; or a combination thereof.

3. The composition of claim 2, wherein the living cell is an insulin- producing cell or a pluripotent stem cell.

4. The composition of claim 3, further comprising a pharmaceutically acceptable diluent or excipient.

5. The composition of claim 1, wherein the network of multi arm polymers is formed from a first functionalized multi arm polymer having a functional group and a second functionalized multi arm polymer having a functional group, wherein the functional group of the second functionalized multi arm polymer is reactive with the functional group of the first functionalized multi arm polymer under physiological conditions.

6. The composition of claim 5, wherein the first functionalized multi arm polymer is a 4-arm 5-10kDa PEG.

7. The composition of claim 5, wherein the first functionalized multi arm polymer is a methacryloyloxyethyl phosphocholine co-polymer that is 100-200 kDa and 60-90% phosphocholine.

8. The composition of claim 7, wherein the first functionalized multi arm polymer is a methacryloyloxyethyl phosphocholine-allylamine copolymer.

9. The composition of claim 5, wherein the functional group of the first functionalized multi arm polymer is a click functional group.

10. The composition of claim 5, wherein the functional group of the first functionalized multi arm polymer is a dibenzocyclooctyne (DBCO) or azide.

11. The composition of claim 5, wherein the second functionalized multi arm polymer is a 4-arm 5-10 kDa PEG.

12. The composition of claim 5, wherein the second functionalized multi arm polymer is a methacryloyloxyethyl phosphocholine co-polymer that is 100-200 kDa and 60-90% phosphocholine.

13. The composition of claim 12, wherein the second functionalized multi arm polymer is a methacryloyloxyethyl phosphocholine-allylamine copolymer.

14. The composition of claim 5, wherein the functional group of the second functionalized multi arm polymer is a click functional group.

15. The composition of claim 5, wherein the functional group of the second functionalized multi arm polymer is a dibenzocyclooctyne (DBCO) or azide.

16. The composition of claim 5, wherein the functional group of the first functionalized multi arm polymer and the functional group of the second functionalized multi arm polymer react to form a triazole.

17. The composition of claim 1, wherein the cell is a mammalian cell.

18. The composition of claim 1, wherein the cell is a human cell.

19. The composition of claim 4, wherein the cell is contained in a syringe or in a biocompatible container.

20. The composition of claim 1, wherein the network of multi arm polymers comprises methacryloyloxyethyl phosphocholine co-polymer.

21. The composition of claim 1, wherein the network of multi arm polymers comprises a combination of PEG and methacryloyloxyethyl phosphoscholine co-polymer.

22. The composition of claim 1, wherein the network of multi arm polymers consists of polyethylene glycol (PEG), a methacryloyloxyethyl phosphoscholine co-polymer, or a combination thereof.

\* \* \* \* \*